US008253778B2

(12) United States Patent
Atsushi

(10) Patent No.: US 8,253,778 B2
(45) Date of Patent: Aug. 28, 2012

(54) THREE-DIMENSIONAL DIGITAL MAGNIFIER OPERATION SUPPORTING SYSTEM

(76) Inventor: Takahashi Atsushi, Fukui (JP)

(*) Notice: Subject to any disclaimer, the term of this patent is extended or adjusted under 35 U.S.C. 154(b) by 65 days.

(21) Appl. No.: 12/933,678

(22) PCT Filed: Mar. 23, 2009

(86) PCT No.: PCT/JP2009/055643
§ 371 (c)(1),
(2), (4) Date: Jan. 21, 2011

(87) PCT Pub. No.: WO2009/116663
PCT Pub. Date: Sep. 24, 2009

(65) Prior Publication Data
US 2011/0102549 A1 May 5, 2011

(30) Foreign Application Priority Data

Mar. 21, 2008 (JP) .................................. 2008-074173

(51) Int. Cl.
H04N 13/00 (2006.01)
G06K 9/00 (2006.01)
(52) U.S. Cl. ........................... 348/42; 382/128; 382/154
(58) Field of Classification Search .................. 382/154, 382/128, 131; 348/42, 61, 77; 434/262, 434/263
See application file for complete search history.

(56) References Cited

U.S. PATENT DOCUMENTS

| 5,748,198 | A | * | 5/1998 | Takeda et al. | 345/441 |
| 8,126,726 | B2 | * | 2/2012 | Matov et al. | 705/2 |
| 2007/0147671 | A1 | * | 6/2007 | Di Vincenzo et al. | 382/128 |
| 2008/0049899 | A1 | * | 2/2008 | Rothschild | 378/86 |
| 2009/0195643 | A1 | * | 8/2009 | Neuman | 348/51 |
| 2010/0086199 | A1 | * | 4/2010 | Kim et al. | 382/154 |

* cited by examiner

Primary Examiner — Jay Patel
Assistant Examiner — Jessica Prince

(57) ABSTRACT

The simulation regarding the state change of the subject in a real space provides a system which represents impacts to three-dimensional computer graphics caused by changes of state of three-dimensional computer graphics composed and fixed to subject, and state of image taking space by simulation, surface polygon model and similar surface polygon model 1 is selected, according to shape pattern, from surface polygon model 2 measures, in a three-dimensional way, subject image existing in the same space, a tracking process is performed on the computer graphics, following to the relative position change of the position changes of the subject and the camera caused in real three-dimensional space, subjects in the visual field of the camera and virtual three-dimensional computer graphics image is unified and displayed by displaying computer graphics image having the same relative position change on the image.

20 Claims, 10 Drawing Sheets

THREE-DIMENSIONAL DIGITAL MAGNIFIER OPERATION SUPPORTING SYSTEM

BACKGROUND OF THE INVENTION

1. Field of the Invention

The present invention relates to a medical navigation operation support system for showing positional relation between a patient body and operational instruments during an operation, in order to improve safety and reliability when approaching invisible areas in a least invasive surgical operation. More specifically, the present invention relates to a three-dimensional digital magnifier operation support system, which displays invisible parts or three-dimensional computer graphics of outward appearance of a solid object (patient body and operational instruments) on top of three-dimensional image of the solid object recognized by a three-dimensional digital magnifier, in order to unify the substantial object image and the virtual three-dimensional computer graphics for recognizing it as a whole in a three-dimensional way.

2. Description of the Related Art

Conventionally, when approaching invisible parts in a surgical operation, internal structure of an object or anatomic image and relative deposition is memorized by observing two-dimensional or three-dimensional image data based on non-invasion inspection data obtained by X-ray, supersonic waves, and magnetism; these memorized image orientation is used together with real field image for performing an operation. Especially in no-bleeding operation such as reposition process for simple bone fracture or joint dislocation, progression of the operation depends on three-dimensional images and finger sensation relying on operator's experience. This delicate three-dimensional sensation of human can be improved by repeated experiences; correctness of the non-bleeding process can be valued only by three-dimensional data obtained after the operation. In additional, in a bleeding operation, when performing an operation on an ill prospect internal environment, the operation may progress to a wrong direction based on a wrong orientation, thus causing unnecessary injury. In order to avoid this risk, it is known that by real-time measuring three-dimensional positions of the patient in operation and operation instruments, and overlaying on top of CT or MRI images took before the operation, even beginners can easily reach the objects, thus improving safety and reliability of the operation. This computer measuring device is not only implemented in Neurosurgery, it is also implemented in fields of head and neck surgery and orthopedic surgery, it is also used for executing MRI, updating images, and performing navigation in the progress of an operation.

BRIEF SUMMARY OF THE INVENTION

Problems that the Invention is Intended to Resolve

As described, however, in the case of using an image-based navigation system, which is implemented upon CT or MRI images took before the operation, a sensing marker is required during the CT or MRI shooting, in order to show the position of the sensing marker on the CT or MRI image, the sensing marker should be mounted on the same position when shooting during the operation, and the three-dimensional position should be measured in real-time. For the sake of correct tracking, as well as sensing marker fixing and reproduction of fixing position, complicated adjustments are required for initial registration of the patient and image positions, and because the real tracking accuracy depends on precision of the sensor, when performing processes on the magnified image, the tracking accuracy increases in proportion to magnifying power of operational field image and in inverse proportion to magnifying power on the monitor.

Therefore, in order to improve position precision and to correct displacement of the sensing marker, MRI shooting is performing during operation, and registration and tracking are performed while updating the images, however, from a real-time viewpoint, because the MRI shooting takes time, this method has time limit, and this is not a favorite situation for a surgery operation.

Basically, all of these navigation systems, however, put the CT or MRI images on the patient position in operation, and display and track the computer graphics of operation instruments; achievements of the operation instruments inside a patient body caused by manipulating the operation instruments are executed based on virtual images shown on a fixed two-dimensional monitor. Accordingly, it is impossible to identify changes in patient's body caused by the operation, and the operator should take his eyes from the monitor to patient's operated area in order to check the patient's condition.

In view of these facts, it is not necessary to fix sensing markers such as infrared rays or magnetism on the patient (object), registration process is performed automatically to unify the relation between the patient position and three-dimensional CG image position, a tracking is performed on relative positional changes of the patient (object) and camera devices and the three-dimensional CG image is overlaid on it, corresponding to movements of the patient during the operation, anatomic three-dimensional CG image of invisible area or three-dimensional CG image of operation instruments overlaid with operation instruments tacking the manipulation of operation instruments are tracked with three-dimensional positional changes of the object, navigation of the operation condition and patient body can be implemented as a real-time image without taking eyes therebetween, in addition, other information of the patient body, such as vital signs, can be checked on the monitor, thus it is not necessary to move eyes from here to there.

Features for Solving the Problems

The present invention is a system providing visual support for invisible area using three-dimensional digital magnifier when implementing medical operation or precise manipulation based on human vision, regenerating real magnification by displaying invisible parts of a current entity.

Generally, when implementing the medical operation or other precise manipulation, a binocular magnification glass is used to perform the operation in order to obtain magnified operation field. For a magnified operation field obtained from an optical magnifier such as this binocular magnified glass worn on head, a pair of monitors is situated in front of eyes of an operator, from a position corresponding to central parts of left and right pupils of the operators in front of these monitors, it is possible to obtain a stereo vision field of the same space using a three-dimensional digital magnifier having a pair of stereo camera toward naked-eye vision field. A situation where the operator can recognize an object visually with naked eyes or optical magnifier can be realized, thus changes of vision direction of the operator and the three-dimensional changes of position of an object can be recognized in a way the same with implementing operation with naked eyes. Accordingly, operations towards an object in the vision field can be implemented by changing position of head, i.e., vision direction, according to natural sensation.

The first embodiment of the invention takes pictures of the subject existing in line of sight using a stereo arrangement camera of the three-dimensional digital magnifier according to stereo method, performs three-dimensional position measurement of pixels constituting the image, the stereo picturing method (stereo vision with two eyes), which performs three-dimensional measurement through triangle measuring distance between 2 stationary cameras, is used for non-contact three-dimensional measurement to acquire the surface polygon model 2 of three dimensional form of the plural subject in the image pickup range. Stereo measurement method, which implements stereo measurement by triangle measuring distance between two fixed cameras, can be binocular stereoscopic vision method, the following method can also be used as a stereo picture three-dimensional measurement method: a stereo method, by way of a spot lighting method causing a spot to radiate through light-emitting diode and to perform a flight time measurement; slit light projecting method, in order to obtain a sectional plane of a subject, light scan is performed using linear light passing a slit with a corresponding point; and pattern light projection method, a pattern, enabling determination of coordinate in the image within the subject, is projected, and depth can be determined accordingly. Basically, a stereo image method is used, wherein a three-dimensional position measurement of pixels in a specific part constituting left and right image is performed, a stereo measurement is performed to execute a triangle measurement to determine distance between two stationary cameras, and then surface polygon model 2 of three-dimensional shape of a subject can be obtained by personal computer processing.

In these methods, it is better to use invisible light as the light sources which do not give impact on eyesight on image on the monitor corresponding to operation object or the organism (subject) serving as an object of image shooting, such as infrared ray. In addition, these light sources is installed in the camera and the three-dimensional digital magnifier, thus in the case that relative position with respect to three-dimensional spaces of the subject is measured and the image of the subject is tracked, the stereo camera receives light projected from a direction the same with the shooting direction of the camera, measurement precision and improving measurement speed can be improved by unifying position complement element of the projector and receiver.

Surface polygon model 1 of each structural component which displays internal constitution from the surface which was separately constructed, in advance, from the operation object or the tomography two-dimensional slice data of the organism is generated. It is a system that distinguishes by way of shape pattern recognized the surface polygon model 1 and the surface polygon model of three-dimensional similar shape form surface polygon model 2, and overlays and tracks virtual three-dimensional volume model computer graphics which was mapped to internal constitution component texture of checked operation object or surface polygon model 1 of the organism. Because this surface polygon model 2 is formed in the image shooting area at the image shooting direction, the respective precision and speed of detection, distinction and tracking process can improve by making the surface polygon model 1 of an object or organism serving as the operation subject, trimming the surface constituting the inner part from the three-dimensional coordinate axis of the subject according to direction of the sight line during the operation, i.e., approaching direction, performing a process in a rejoin the same with the camera visual field at initialization, or a smallest region comprising a feature land mark, and reducing number of the constituting polygon as more as possible. In the three-dimensional digital magnifier visual field of the operator, virtual three-dimensional volume model computer graphics, mapping on internal constitution component texture being linked and tracked with the non-displayed surface polygon model 1, is synthesized and presented on the front operation field existing in the visual field. It is clear that, at this time, the polygon shapes constituting these surface polygon model 1 and surface polygon model 2 is unified.

As described, by three-dimensional volume model computer graphics overlaying partial or whole entity image, the internal constitution invisible area of the subject presented in the three-dimensional digital magnifier can be identified as internal constitution component image of the virtual three-dimensional volume model computer graphics at the same visual three-dimensional position in the image shooting space of the subject. The same as the manipulation of the subject existing at sight, the three-dimensional volume model computer graphics, visually recognized at the same position in a three-dimensional space as the subject at sight, can be manipulated, by hand, directly or indirectly.

Furthermore, during the operation, this virtual three-dimensional volume model computer graphics tracks the relative three-dimensional position change of the camera and the subject in the image shooting space, and changes, in real time, display layout, thus a three dimensional digital magnifier actual operation support system generating high real-time interaction is constituted. In a case that all components are displayed for anatomy components being constituted by sectional two-dimensional slice data, i.e., volume model, only outer constitution components are recognized in this virtual three-dimensional volume model computer graphics overlaid with the subject.

In a second embodiment, the left and right camera and image display device of the three-dimensional digital magnifier are arranged in parallel and used as individual component, instead of using the three-dimensional shaped surface polygon model 2 constituted from stereo measurement using the described camera of the three-dimensional digital magnifier. By mapping and tracking contour or feature point or line constituting the surface polygon model 1 of each constitution component established, in advance, from two-dimensional slice data of operation object or organism obtained by tomography to the image data taken by respective left and right camera of the three-dimensional digital magnifier, any one of the three-dimensional computer graphics of each of the internal constitution mapping to the internal constitution component texture within the surface polygon model 1 is match moved to subject image displayed on the respect left and right binocular vision image display device, simulation corresponding to state change of the subject of image taking in real space is represented as simulation, which presents: state of three-dimensional computer graphics corresponding to internal constitution of subject of image taking, which is displayed with presence, i.e., just as floating on the image taking space, through angle of binocular disparity which is overlaid and displayed upon the subject of stereo vision by the three-digital magnifier, and indirect impact on three-dimensional computer graphics caused by state change of the image taking space.

In the third embodiment, in order to identified these internal elements visually, virtual three-dimensional computer graphics overlay on a subject within an image shooting space is, in response to applications, categorized according to structural or anatomical constitution elements, and is recorded as respective layer, the respective layer can be displayed individually or selectively composed according to depth reached by operation instrument during operation or other conditions during operation. Using mandibular bone dental implant operation utilizing this system as an example, virtual three-dimensional computer graphics image of the mandibular bone cortical bone, as an mandible anatomical constitution element, is tracked and displayed to image within mandibular oral cavity in the visual field of the three-dimensional digital magnifier in a substantial space, thus before the gum is cut open from above, form of the alveolus bone can be identified three-dimensionally. Therefore, it is possible to select a region with sufficient bone quantity, to select access direction from correct position, thus hemorrhage caused by incision would not occur and is useful for preventing edema after the operation. After an access hole was formed on the cortical bone by a pre-processing, three-dimensional computer graphics layer of the cortical bone of bone body in the mandibular bone is made non indicatory, and three-dimensional computer graphics layer of lower alveolus nerve is arranged in relative fixed position against the subject, and the access hole form on the subject is used as a guide entry, when a drilling punching is performed on the subject, based on three-dimensional visual recognition, after removing danger of nervous damage, in order to support occlusion power implant burying entrance fossa is formed as deep as possible, and this high-level operation technology can be implemented safely and precisely. Selective indication of these layers simulates not only anatomy element, as the guide for drilling accurate implant fossa hole on three-dimensional computer graphics of the mandibular anatomy component which was drawn up from the DICOM data on a relatively fixed position. In the case that the subject image is made non indicatory, patient subject, which is displayed three-dimensionally on the substantial space in front of the operator on three dimensional digital magnifier monitor in a way the same with naked eye visual field or visual field of optical magnifier, and virtual three-dimensional computer graphics, which is displayed on the same three-dimensional position, are identified visually, operation can thus be implemented with identification of virtual computer graphics image, which makes internal structure that cannot be visually identified by subject image through transparency conversion or coloration of outside layer, and tactile sensation, which is generated when operator stretches his arm and touches the subject, with unified sensation the same with performing operation by sensation from direct touch while visually recognizing subject at sight.

Furthermore, operation for the apparent region may be performed safely and accurately, since internal constitution information can be obtained in more details compared to performing operation by observing the subject image.

Conventionally, in a case that operation is performed using stationary sensor and monitor, operator is forced to perform the operation in an unnatural way by gazing at the monitor instead of the patient (the subject), when line of sight is to be changed, the patient (the subject) is required to move, or sensor position is required to be changed. On the contrary, according to this invention, the operator can perform operation on the patient, being visually identified at a direction the visual field of the naked eye, through direct sensation, the same with the situation where the device is not installed corresponding to changes of gaze modification of the operator and change of physical condition of the patient, the visual three-dimensional relative position relationship in the substantial space is maintained, thus operation can be performed through natural sensation.

In addition, the fourth embodiment, as a method to improve visual recognition of three-dimensional computer graphics categorized according to the anatomy component, provides a three-dimensional digital magnifier magnifying real operation support system of embodiments 1, 2, and 3, wherein: in order to improve visual recognition of the shot image and composed image, shot image or three-dimensional computer graphics, or a composed image position complement tracking is performed to improve visual recognition by setting difference to image data of object, serving as a subject of operation, displayed on the three-dimensional digital magnifier of the operator or organism, which comprises performing image processing on at least one of elements of hue, chrome, lightness, shading and lighting direction, or overlay processing comprising transparent mapping, hidden line elimination wire frame, blinking representation. By doing so, even in a situation where three-dimensional computer graphics image represents internal structure of a shot object in a substantial space recognized, three-dimensionally and visually, by three-dimensional digital glasses, visual identification with more clarity is possible. Furthermore, like the third embodiment, visual identification can be further improved by performing image process on the respective layer constituted by each anatomy component. In addition to improvement of the visual identification of the image, it is possible to visually recognize the anatomy component at one glance. Using an operation removing affected part as an example, while large blood vessel and the nervous bundle are simultaneously recognized, visually and three-dimensionally, it is possible to approach the affected part safely, and in a shortest distance through the three-dimensional recognition, thus surgical invasive attacking is limited to minimum level.

Three factors of magnification reality are real-time interaction, self projection, and three-dimension space. In the case where manipulation is performed by wearing the three-dimensional digital magnifier as described, the virtual three-dimensional volume model computer graphics performs a real time tracking according to relative three-dimensional position change of the operator and the subject, thus real time interaction occurs, without time lag, between the subject and virtual image. Furthermore, three-dimensional digital magnifier, three-dimensionally arranging image taking device with left and right binocular disparity with identical angle, and presenting image on an image display device set in front of left and right eyes using parallel method or intersection method, enables three-dimensional identification of operational space, maintains three-dimensional space characteristics, virtual computer graphics, tracking and rendering on operated object or organism on the three-dimensionally identified operational space, is also constituted by three-dimensional volume model, thus the operator can identify, in a stereo way, the whole visual field of the three-dimensional digital magnifier. The operator can stretch his hand on and perform operation on operated object or organism at sight, in a way the same with implementing the manipulation by hand and naked eyes, with no conscious of the installation of three dimensional digital magnifier, his own hand existing in the operation field space corresponding to the virtual three-dimensional volume model computer graphics can be projected as a substantial image within the visual field of the three-dimensional digital magnifier.

The stereoscopic vision using left and right image display devices of three-dimensional digital magnifier comprises: parallel method, wherein right image is observed by right eye, and left image is observed by left eye; and intersection method, wherein right image is observed by left eye, and left image is observed by right eye, i.e., gaze crosses before the image. The intersection method has an advantage that the size of the image can be magnifier more than parallel method does. In addition, it is known that, physically, women have weak stereoscopic vision, and for women, the intersection method is easier to perform than the parallel method. It should be note that, in the present invention, method for presenting the left and right images and method for presenting the virtual computer graphics on left and right monitors may be changed in response to application condition. In fifth embodiment, however, image of the stereo-arranged camera is respectively displayed on a pair of binocular visual image display device, virtual three-dimensional volume model computer graphics is represented as over layer on image display device of one side of the three-dimensional digital magnifier monitor enabling stereo vision of subject image through left and right angle of binocular disparity, by doing so, the stereo presented invisible are of internal structure of the subject displayed on visual field of three-dimensional digital magnifier is represented by image of internal constitutional element of the virtual three-dimensional volume model computer graphics.

In this system, virtual three-dimensional volume model computer graphics is represented as over layer on image display device of one side of the three-dimensional digital magnifier monitor enabling stereo vision of subject image through left and right angle of binocular disparity, by doing so, the stereo presented invisible are of internal structure of the subject displayed on visual field of three-dimensional digital magnifier is represented by image of internal constitutional element of the virtual three-dimensional volume model computer graphics. At this time, in the case that ratio of the virtual three-dimensional volume model computer graphics of operated object or organism occupied the whole visual field increases, the operation visual field, as a background image, can represent the shot image of one effective side on the monitor of both eyes, or simply represent the virtual three-dimensional volume model computer graphics of the organism on left and right monitor of the three-dimensional digital magnifier. Especially, when magnification ratio is high, shape pattern detection is performed on surface polygon model 1 of organism and surface polygon model of three-dimensionally similar shape with real ratio of the camera, the whole image displayed by the three-dimensional digital magnifier is mapped, three-dimensionally, to surface polygon model 1 of organism, it can also be represented by virtual three-dimensional volume model graphics. Quality of the display image depends on the virtual three-dimensional volume model graphics, thus, it is not necessary to consider image quality deterioration caused by hardware function in a case of high magnification ratio, only the anatomy element which is required for the operation is deformed and regenerated in the virtual three-dimensional volume model computer graphics, thus providing simple visual information of high quality to the operator. When using three-dimensionally presented high quality virtual three-dimensional volume model computer graphics, by displaying single image on left and right image display device of the three-dimensional digital magnifier, reality in front of the operator can be identified from the three-dimensional virtual image. Similarly, when displaying operation field image information of the image pickup device of effectiveness eye side of three dimensional digital magnifier of the image pickup device of the stemma on the image display device of the same side, and displaying three-dimensional computer graphics image with depth on the monitor of the opposite side, by doing so, the subject image can be identified, in a magnified way, as a three-dimensional original image. In this situation, in a case that the position of camera excludes a position with limited visual field caused by barrier of cheek and lip, for example, inside the oral cavity, man used to catch an object set on a position at the sight line of the effective eye, thus it would be better to set the camera in front of the monitor on the side of the effective eye.

In addition to the detection with shape pattern identification of the surface polygon model of first embodiment, in the sixth embodiment, two-point measurement is performed, using stereo camera, on four markers set at any position of the subject in the image data of the stereo-arranged camera of the three-dimensional digital magnifier according to optical or digital magnifying ratio of the three-dimensional digital magnifier, a three-dimensional position measurement of the three-dimensional surface polygon model of the subject is performed from the distance between the camera and the subject, and scale of stereo measurement surface data recognition is changed, after image of the subject or the organism is selective detected, mapping and real time tracking is performed on the three-dimensional volume model computer graphics, display position, direction and size of patient anatomical CG and subject (operation instrument CG) are changed, thus is composedly displayed on left and right image display devices of the monitor of the three-dimensional digital magnifier. Accordingly, display position, direction and size of the patient anatomical CG and subject (operation instrument CG) are changed to fit the scale of the surface polygon model of operated subject or organism, i.e., the original identified data, thus the identification and mapping precision corresponding to image of operated subject or organism can be improved, and time lag of real time tracking can be reduced.

In addition, it is possible to obtain stable mapping base point, by utilizing the marker of sixth embodiment even the occasion where second embodiment is executed.

When implementing the first and second embodiment, just like the seventh embodiment, a target subject positioned in invisible region can be easily identified, by representing direction of visual field, where three-dimensional computer graphics volume model of a subject or an anatomic specific part of the patient outside display range of monitor of the three-dimensional digital magnifier exist. The visual representation is implemented by an arrow or blinking edge of the image. In addition, especially in the case that high digital magnifying ratio is implemented; part of the subject or organism is displayed in the three-dimensional digital magnifier image on the monitor according to the magnifying ratio. In this situation, the direction, in which the subject or the anatomic specific part of the patient outside display range of monitor of the three-dimensional digital magnifier within the three-dimensional graphics volume model, is represented by causing edge of the image display to blink, or by displaying direction indicator with an arrow, or by showing a frame enclosing image of the displayed portion in entire image wherein the whole is scaled down and displayed in the cutoff screen, thus position relationship of target portion and visual field portion during the operation can be identified, and operation target portion of three-dimensional computer graphics image corresponding to tracking subject or organism is detected.

In the eighth embodiment, any of the CG volume model with registration layout and match move on respect patient subject is fixed on a position corresponding to a specific CG volume model at any position upon the movement tracks, in order to using this in visual positional evaluation of operated position, direction, and angle, when using the system of the first and second embodiments, in the case that each patient anatomical CG volume model, being connected by joint or tissue with registration layout and match move on patient subject upon the three-dimensional digital magnifier, is moved, any of the CG volume model with registration layout and match move on respect patient subject is fixed on a position corresponding to a specific CG volume model at any position upon the movement tracks, and thus can be unified and moves together with the specific CG volume model match moving with the patient subject. Generally, in an operation performed in an oral cavity with limited space, especially in a dental implant operation, if not in a mouth-opening state, it is difficult to form implant indentation by inserting drill in contra angle of hand piece. At this time, CG volume model of mandible in an occlusion state is matched and moved according to maxillary CG volume model, the operated subject, because the insertion space for the instrument is reserved during the operation, even in a mouth-opening state, the occlusion state of opposing teeth can be visually identified through the virtual mandible CG volume model, thus the opposing relation can be three-dimensionally identified and suitable surgical guide can be provided. Using this system, in a case in which a patient subject is incised, cut, and cut off by operation instruments and a shape change is generated accordingly, not every thing would be reflected in the virtual three-dimensional volume model computer graphics. This virtual three-dimensional volume model computer graphics is useful in comparing with the state before operation, by regenerating state during and after operation on the virtual three-dimensional volume model computer graphics, the whole operated subject can be substituted by the virtual three-dimensional volume model computer graphics. In order to enabling this visual representation, in the ninth embodiment, an operation instrument CG volume model, being processed by registration layout and match move to the operation instrument, is processed by Boolean operation against patient anatomical CG voxel volume mode, patient anatomical CG volume model with registration and match move to the patient subject is processed to incorporate a visual change the same as the operated subject and to display subject invisible part in the patient anatomical CG volume model. In addition, similar to the situation where implant indentation is formed by drilling bone, image information represents invisible region of subject on the patient anatomical computer graphics volume model, thus depth or angle reached by instruments inside the operated subject, which cannot be identified by naked eyes, can be identified on the patient anatomical computer graphics volume model image, and can be displayed on the patient anatomical computer graphics volume voxel volume model as a visual shape change the same identical with the changed implemented on the subject.

The three-dimensional volume model computer graphics of each anatomical constitution components can represent internal structures by making outside anatomy components transparent, and by implementing coloration in order to present plural constitutions, but it may introduce confusion when identifying complex computer graphics constitution comprising several layers. In order to avoid this problem, the tenth embodiment, when using the systems of first and second embodiments to perform operation, any surface model which is fixed at three-dimensional digital magnifier or area indicator area (wire frame, translucent coloration indicatory or transparency) is overlaid against a patient anatomical CG volume model, in which distance between the three-dimensional digital magnifier and the patient is processed by registration layout and match to a patient subject on the monitor of the three-dimensional digital magnifier, the overlaid part is trimmed off by Boolean operation, cross section of the patient anatomical CG volume model is displayed using preset sectional display range as a unit, or the cross section of the patient anatomical CG volume model, in which processed range changes according to a preset distance between the three-dimensional digital magnifier and the patient is displayed, in real time.

In the eleventh embodiment, the operation instruments of the operator wearing the three-dimensional digital magnifier of the ninth embodiment is used, the operation instrument CG volume model, and virtual three-dimensional volume model computer graphics, presenting changes the same as the subject comprising invisible area of the subject by the operation instrument CG volume model, virtual three-dimensional volume model computer graphics, representing cross section of patient anatomical computer graphics voxel volume model displayed by the preset cross section, or representing cross section, which is taken according to voluntarily set distance between three-dimensional digital magnifier and patient subject, data is transferred to personal computer in a state, wherein relative position of each of the virtual three-dimensional volume model computer graphics displayed by the operator three-dimensional digital magnifier is remained, the virtual three-dimensional volume model computer graphics, maintaining the respect relative position displayed on the personal computer monitor or three-dimensional digital magnifier, is displayed as tilt, pan, zoom, freely revolution in six revolution axis, by doing so, observation can be performed on condition of subject space from a direction different from operation's gaze.

Furthermore, in the $12^{th}$ embodiment, while identifying tracking and rendering image information of virtual three-dimensional volume model computer graphics obtained by causing the operator's visual field or the virtual three-dimensional volume model computer graphics to be revolved three-dimensionally by image processing executed by personal computer mounted on head mount display of the operation helper, it is caused to move freely, using an interface capable of controlling arbitrary surface model area (wire frame representation, translucent coloration representation or transparency) at six axis, and the same image processing of personal computer is implemented on the overlaid portion, and is trimmed off by Boolean operation, cross section of the virtual three-dimensional volume model computer graphics may be represented accordingly. By presenting, simultaneously, cross section of the arbitrary virtual three-dimensional volume model computer graphics controlled by the helper on virtual three-dimensional volume model on the image display device of three-dimensional digital magnifier of the operator, a third party implements visual instruction, with presence, displaying visual instruction image on an operator visual field stereo image.

As described, in the virtual three-dimensional volume model computer graphics maintaining respective anatomical constitution components, especially in a case that, such as the tooth, a rigid body comprising connecting dental crown and dental root and a portion (dental root) of it is buried in the jawbone, when using the first and second embodiments, state of dental root within the jawbone can be identified three-dimensionally without bleeding, thus it is useful for wire bending for avoiding dental root absorption and tooth drift speed delay caused by interference of the dental root. In addition, in the $13^{th}$ embodiment, surface polygon model 1 of tooth (the crown, dental root), jawbone and maxillofacial, individual parts, which is established from two-dimensional slice data, of operation object or organism obtained beforehand by tomography, is stored respectively, surface polygon model 2 of the individual parts is overlaid on the surface polygon model 2, which measures, by stereo method, the tooth (crown) and oral cavity, and maxillofacial shot by three-dimensional digital magnifier, after surface polygon model 1 of individual parts of the surface polygon model 2 on the front visual field image of the three-dimensional digital magnifier and surface polygon model with three-dimensionally similar shape are detected by respective shape pattern, by performing a tracking on the virtual three-dimensional volume model computer graphics of respective tooth (the crown, dental root) and jawbone which are texture mapping to the polygon model 1, a state of jawbone and tooth and dental root remaining in the jaw bone within an invisible part under an inner mucous membrane within the oral cavity is visually and three-dimensionally recognized using the three-dimensional digital magnifier image display device, and the dentition is recorded as the three-dimensional computer graphics. By recording and storing the chronological changes of respective tooth as virtual three-dimensional volume model computer graphics data of image display device of three-dimensional digital magnifier, by representing storage data of virtual three-dimensional volume model computer graphics of tooth recorded at a previous treatment, the chronological changes of tooth movement can be three-dimensionally identified, just as a time machine, thus it is useful for evaluation of treatment efficiency and reconstructing treatment plan. The storage of virtual three-dimensional volume model computer graphics covers all shape changes, and is useful for evaluating treatment. In addition to treatment evaluation referring to the pre-operation record, in the $14^{th}$ embodiment, virtual three-dimensional volume model computer graphics voxel model constituted from two-dimensional slice data of operated object or organism is computer surgery (re-constituted) to state of treatment target (V.T.O.), and is mapped and displayed on the subject image, by doing so, the treatment target can be identified. In this application, when performing orthopedics treatment of mandibular protrusion, virtual three-dimensional volume model computer graphics voxel model of mandible bone after the treatment is generate, in advance, by computer surgery, when it is mapped to the mandible bone (operated object), regeneration can be easily implemented by identifying, using the V.T.O., the occlusion with positioning is easy to become unstable after disjunction of the left and right gnathal joint. In orthodontic treatment, when the ideal arch form of teeth alignment image of treatment target re-constituting three-dimensional volume model computer graphics of respective tooth of the $10^{th}$ embodiment is represented in oral cavity displayed on the monitor of three-dimensional digital magnifier, treatment steps towards the treatment target (V.T.O.) can be established precisely and efficiently.

In the $15^{th}$ embodiment, texture of a size gauge is mapped to virtual three-dimensional volume model computer graphics voxel model constituted from two-dimensional slice data of operated object or organism. The size gauge is directly represented, just as contour line, on the surface of anatomical constitution components, thus facilitating visual three-dimensional identification of shape. Support for correct operation can be provided by displaying the size gauge of cross section display formed in the 10th and $12^{th}$ embodiments. In addition, operation with higher three-dimensional precision can be implemented by representing virtual three-dimensional volume model computer graphics voxel converted to transparency state with square cube texture. The size gauge is not only applied to organism or operated object, in a dental implantation operation, concentric circle or sphere, or rectangle size gauge is mapped to operation instruments such as cutting drills, distances from adjacent tooth or anatomy landmark can be determined during operation. In addition, preset three-dimensional computer graphics surgical guide of line or image representing three-dimensional approaching direction of the instrument against invisible region of internal structure is overlaid on object or organism, which serves as an operated object, and instruments, by doing so, the approaching direction of instrument against the object or organism can be easily identified, thus operation such as bone cutting operation can be implemented.

The $16^{th}$ embodiment provides a three-dimensional digital magnifier magnifying real operation support system, wherein: using the system of the first and second embodiments, left and right indirect head of the mandibular bone CG volume model with registration layout and match move to the mandibular bone, which is linked by a straight line of virtual butterfly axis, is caused to move, cross sectional line of left and right head of mandible with no position change of persisitens during movement of the virtual butterfly axis is checked on the monitor, at the same time, center of mandible head is determined by setting the cross sectional line, mandible movement from this center is checked on the monitor, locus in accurate condyle path angle is shown in graphic on the monitor, virtual occlusion vessel is established on the monitor by recording the mandible movement as three-dimensional data. The regenerated record constituted virtual occlusion vessel on the personal computer, when using the virtual occlusion vessel to implement design of prosthetic appliance, precise occlusion function restoration much better than the conventional cinema check occlusion vessel can be realized.

In the first and second embodiments, internal structure of a subject is visually identified by overlaying and displaying virtual three-dimensional volume model computer graphics image on an image of the subject, while in the $17^{th}$ embodiment, front visual field shot image is made non-indicatory on the image display device of the three-dimensional digital magnifier of the first and second embodiment, only virtual three-dimensional volume model computer graphics image tracking shot operated object or organism (subject) image is represented. In the first and second embodiments, three-dimensional relative position of subject and three-dimensional digital magnifier worn by an operator shall regenerated on the virtual three-dimensional volume model computer graphics image, therefore, when the operator utilizes visual identification, just like the subject, of virtual three-dimensional volume model computer graphics in the image display device of three-dimensional digital magnifier, and direct or indirect tactile sensation on the shot operation subject object or organism (subject), operation can be performed on the shot object=subject, in a way just like directly observing the shot image of the subject. This is because man is the subject in manipulation within hand reachable range, head position and visual field of this man is the same with the situation where manipulation is implemented by naked eyes (as well as the situation of using glasses or optical magnifier), with natural sensation complete different from the conventional manipulation wherein operator watches a desk-top monitor and manipulates a portion at different gaze, this embodiment can be applied clinically in a short time. Especially in an operation using high magnification ratio, visual identification can be implemented easily by and deformering and representing anatomical constitution elements of virtual three-dimensional volume model computer graphics. In a case that visual field of an operator is complemented by virtual three-dimensional volume model computer graphics tracking organism (subject) image, shot operated object or organism (subject) would not give impact on the vision of the operator, thus a passive stereo method by spot lighting method, wherein a spot radiates through a light-emitting diode; or an active stereo method comprising slit light projection method for obtaining shape of the subject by scanning light in order to obtain cross section of the subject by linear light passing a slit generating a corresponding point, or pattern light projection method for determining depth by projecting pattern enabling determination of coordinates of the subject within the camera image can be implemented, thus shortening measuring time and improving processing speed.

In the 18$^{th}$ embodiment, image data stores respective layer, no matter whether substantial space image of the left and right image taking devices, and three-dimensional computer graphics image data is represented or not on the subject image, in addition to the substantial space image of the left and right camera. When using a three-dimensional display monitor for the record of substantial space image, three-dimensional record image may be provided, not limited to HMD. In addition, when three-dimensional computer graphics image is regenerated from record, it moves with the subject image and is displayed as three-dimensional animation, the respective layer image is output individually or selectively composedly, and is displayed on three-dimensional digital magnifier or general monitor, three-dimensional computer graphics record data maintaining time-dependent form change is presented on the monitor in a way enabling free manipulation of tilt, pan, zoom and revolution in six revolution axis, thus it is possible to evaluate operational progression from a view point which can not be observed by the operator. The virtual three-dimensional volume model computer graphics, presenting changes the same as the subject comprising invisible area of the subject by the operation instrument CG volume model of the 11$^{th}$ embodiment can be further evaluated from arbitrary view point change. The data storage can realize the same effect as the chronological fragment data recording and storage, thus it is useful for evaluation of long-term treatment such as orthodontic treatment, in a case that components of bone growth is reflected and evaluated in record data, it is useful for identification of bone growth center, thus it is useful for determining treatment plan based on growth prediction.

The present invention provides operation support by computer graphics image processed, in real time, according to three-dimensional image of subject, wherein shading is important for improving representation of computer graphics image. In the 19$^{th}$ embodiment, the whole three-dimensional computer graphics image scene, using image on subject space covered by subject image of two-dimensional digital magnifier camera as a background, three-dimensional computer graphics image and internal structure thereof, as virtual reality, is processed to make photo real composition image using the two-dimensional image as a light source for lighting, therefore, enabling magnification with high reality sensation.

In the 20$^{th}$ embodiment, when the substantial space image of the left and right camera and three-dimensional computer graphics image frame is shown alternatively, the respective number of presented frames is adjustable, in the case of overlay representation, the representation ratio, corresponding to left-shot image, right-shot image, or the three-dimensional computer graphics image, of the left and right monitors of the three-dimensional digital magnifier is adjustable, thus image binocular visual identification is adjustable. Compared to the image shown at the effective eye, the image shown at opposite eye represents object with lower identification level, accordingly, using this fact, by generating difference in vision clearness of the image displayed on left and right monitors, identification ratio of image display can be adjusted in order to easily modify the identification ratio according to effective eye and opposite eye owing to personal preference. Accordingly, magnified real space generated from three-dimensional image can be easily observed from three-dimensional digital magnifier immediately when wearing the device from naked eyes.

The following effects can be obtained by the described features.

Effects of the Invention

According to three-dimensional digital magnifier magnifying real operation support system of claims 1~19, shot object existing in the same space is detected and identified from surface polygon model 2, and cross sectional imaging two-dimensional slice data surface polygon model of shot object and three-dimensionally similar surface polygon model 1 is identified by shape pattern identification, by tracking virtual three-dimensional volume model computer graphics which maps texture to the surface polygon model 1, by following the relative position changes between the image subject and the camera occurred in a real three-dimensional space, the entity, i.e., the image subject within the visual field of the camera, and virtual three-dimensional computer graphics image is unified, in the visual field of the camera, the image subject and three-dimensional computer graphics image are unified and displayed independent to the special position changes corresponding to the image subject and camera, therefore, the respective layer of three-dimensional computer graphics image constituting each anatomical constitution components is displayed selectively or after processed by prospective-transparent process on the shot image, by doing so, it is possible to correctly approach invisible portion inside a subject at sight, while identifying internal structure, without relying to uncertain estimation generated from experience or sensation, through vision of virtual computer graphics image which visualizes internal structure which can not be identified by subject image, with sensation the same with the situation in which operation is implemented by direct sensation by hand and visual identification of subject at sight.

In addition, according to the second invention, left and right camera of three-dimensional digital magnifier and image display devices are aligned and constituted respectively, by doing so, by tracking and match-moving, respectively, subject image, displaying on binocular image display device, of arbitrary three-dimensional computer graphics of respective internal constitution component mapping texture of constitution components of internal structure, different three-dimensional computer graphics of internal structure of subject can be overlaid and displayed on subject image displayed on the left and right image display device of three-dimensional digital magnifier, accordingly, magnification with reality can be provided to the operator through stereo identification with high quality, as a prospective image with presence, just like melting into subject image in shooting space by way of binocular disparity angle.

In addition, in a case in which a subject (patient subject) is incised, cut, and cut off by operation instruments and a shape change causing volume change is generated accordingly, an operation instrument CG volume model, being processed by registration layout and match move to the operation instrument, is processed by Boolean operation against patient anatomical CG voxel volume mode, patient anatomical CG volume model with registration and match move to the patient subject is processed to incorporate a visual change the same as the operated subject and to display subject invisible part in the patient anatomical CG volume model.

Furthermore, by processing the virtual computer graphics image, three-dimensional visual guide marker or animation can be added, thus operational efficiency can be improved and operation with high precision can be implemented. These processed three-dimensional computer graphics image and all of the described layers of the computer graphics image can be recorded and stored respectively. Accordingly, it can serve as useful basis for evaluation of chronological changes and predictive estimation.

BRIEF DESCRIPTION OF THE DRAWINGS

The present invention can be more fully understood by reading the subsequent detailed description and examples with references made to the accompanying drawings, wherein.

DESCRIPTION OF SYMBOLS

Figure 1:
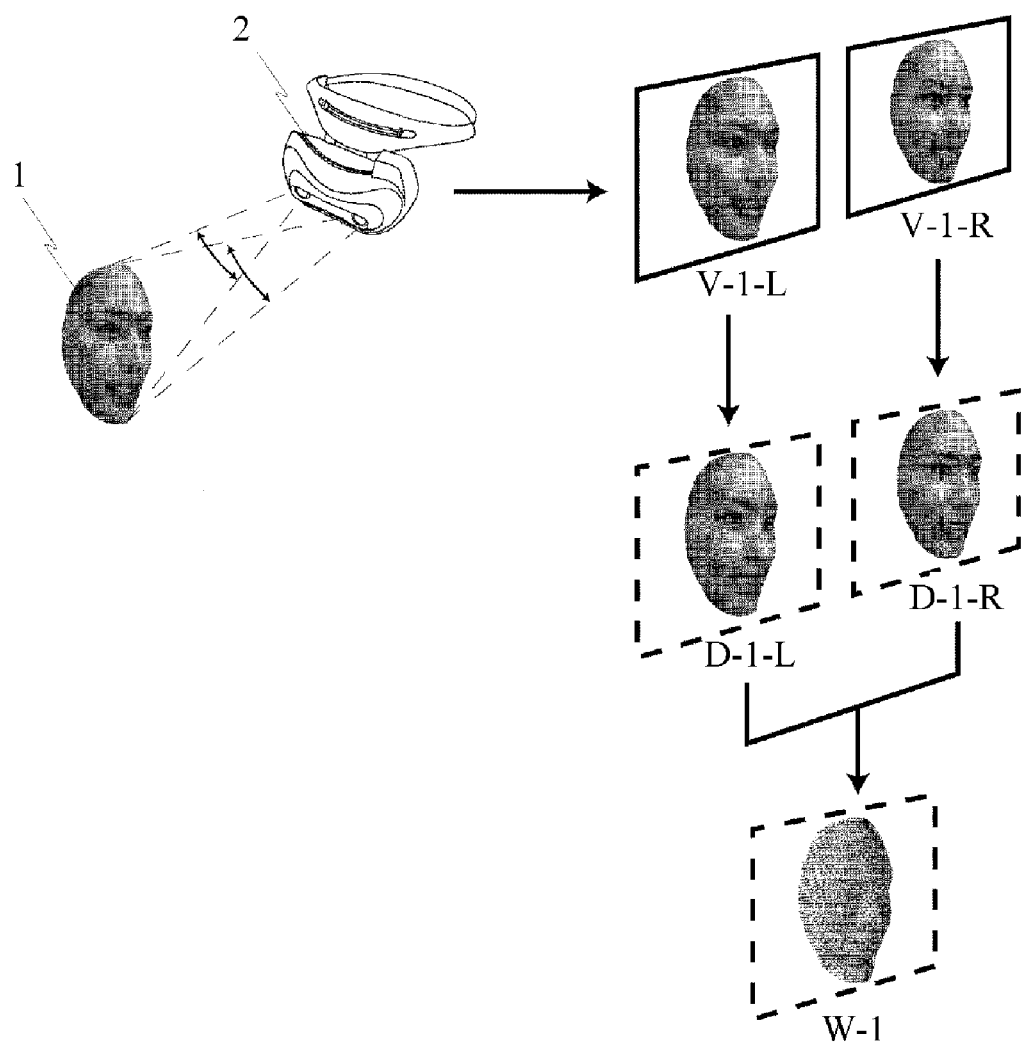
FIG. 1 shows construction of a surface polygon model W-1 using stereo image V-1-R, V-1-L, and left-hand and right-hand image data D-1-R, D-1-L displaying on a three-dimensional magnifier.

1、 object (face, skull)
2、 three-dimensional digital magnifier
3-a、 perspective line
3-b、 perspective line
3-c、 perspective line
3-d、 perspective line
3-e、 perspective line
4、 tooth
4-C、 tooth CG
4-C、 dental root CG
4、 facial soft tissue CG
7、 mandible bone CG
8、 skull bone CG
9、 gum soft tissue
9-C、 gum soft tissue CG
10、 cortical bone
10-C、 cortical bone CG
11、 spongy bone
11-C、 spongy bone CG
12、 neural tube in dental alveoli of mandible
12-C、 neural tube in dental alveoli of mandible CG
13、 motor
14、 cutting drill
14-B、 implant indentation CG
14-C、 cutting drill CG
15-C、 surgical guide CG
16、 ideal arch
16-C、 computer graphics ideal arch
17-C、 computer graphics hinge axis
18-C、 computer graphics hinge arc
19-R、 virtual right pantograph flag X axis plane
19-L、 virtual left pantograph flag X axis plane
20-R、 virtual right pantograph flag Y axis plane
21-L、 virtual left pantograph flag Y axis plane
21-R、 virtual right pantograph flag Z axis plane
21-L、 virtual left pantograph flag Z axis plane
22、 critical path of mandibular incisor
23、 moving track of center of caput mandibulae
24、 virtual bracket position CG
25、 virtual articulation plane CG
26、 labia oris
27、 vision marker
C、 surface data computer graphics of anatomical elements of head
C-1、 computer graphics of skull bone
C-2、 facial surface polygon model
C-3、 facial computer graphics
D-1、 three-dimensional digital magnifier image data
D-1-R、 three-dimensional digital magnifier right image data
D-1-L、 three-dimensional digital magnifier left image data
D-2、 three-dimensional measurement (CT) polygon surface model
V-1、 three-dimensional image
V-1-R、 three-dimensional digital magnifier right image data
V-1-L、 three-dimensional digital magnifier left image data
V-2、 object and bone CG overlapping image
V-3~V-6、 soft tissue CG、bone CG overlapping image
V-7~V-9、 dental alveoli of mandible substantial image
V-10~V-12、 gum soft tissue CG, cortical bone CG, spongy bone CG, neural tube of dental alveoli of mandible CG, and cutting drill, implant indentation CG, cutting drill CG overlapping image
V-13~V-15、 gum soft tissue CG, cortical bone CG, spongy bone CG, neural tube of dental alveoli of mandible CG, and cutting drill, implant indentation CG, cutting drill CG、surgical guide CG overlapping image V-16~V-18、 gum soft tissue CG、 cortical bone CG
、 spongy bone CG 、neural tube of dental alveoli of
mandible CG、 cutting drill, implant indentation CG
、cutting drill CG、 surgical guide CG overlapping
image and perspective section V-19、 computer graphics ideal arch 、mandible bone CG
overlapping image W-1、 facial surface polygon model (generated from
three-dimensional digital magnifier image data)

DETAILED DESCRIPTION OF THE INVENTION

Best Modes for Implementing the Invention

Here, description of the embodiments of the present invention is provided referring to the accompanied drawings.

FIGS. 1~10 represent exemplary elements and embodiments of the present invention. Frames in the drawings represent monitor image of a digital magnifier, recognized image of a monitor or an image on PC monitor. The thing showing three-dimensional representation by the right and left monitors is accompanied with the digital magnifier monitor. In addition, the parts which are labeled with the same symbols represent the same thing.

The working principal of the three-dimensional digital magnifier constituting the present invention is, when images projected on retina by human eyes are identified by the brain, a living system identifying distances using angle of parallax of left and right eyes is manipulated, a three-dimensionally identified condition is reproduced by vision on an image display device positioned in front of left and right eyes. In other words, stereo-camera device, which is positioned in front of left and right pupils of three-dimensional digital magnifier, functions as user's eyes, i.e., as crystalline lens at the first part of vision recognition system. By representing, respectively, left and right image data on left and right image display devices, the user can recognize things three-dimensionally in a way the same with watching things with his naked eyes. Using a three-dimensional digital magnifier functioning according to this principle, an operator can recognize a pictured object as a three-dimensional image by projecting images taken from different direction on right and left display devices V-1-R and V-1-L. The left and right two-dimensional image data D-1-L, D-1-R utilized in binocular-stereo-vision functioning as two eyes is processed by stereo image method to produce a surface polygon model W-1, wherein the method executes a calculation using changed angles of stereo-positioned left and right camera devices, and triangle measurement data obtained from distances between two fixed cameras to perform a stereo measurement. The surface polygon model W-1 has the same view point (the same camera device) as the substantial image shooting, thus no adjustment is required. Relative position in three-dimensional space of the object (solid object) and three-dimensional digital magnifier camera device (operator) is shown, and it can be unified with the solid object image, thus no adjustment process is required. The picture taking range of the image taken by these camera devices is determined by distance between object and camera device, and magnifying factor of the camera device. Nevertheless, in a case where the magnifying factor is determined to meet requirements, from the viewpoint of ergonomics, working length is a operational distance in a range of 10 cm~40 cm from the operator according to an ergonomics view, a measured point set for initialization is a position at the nearest proposed working length. In a case that lips or cheek in an oral situation cannot be set as an image of a measured point at initialization, an initiation process is performed for a measured point in a visible area, and dentition or a firm point of teeth in an inner side of the measured point, i.e., inner side of lips and cheek, and thus precision of stereo measurement for magnified display is improved.

Figure 2:
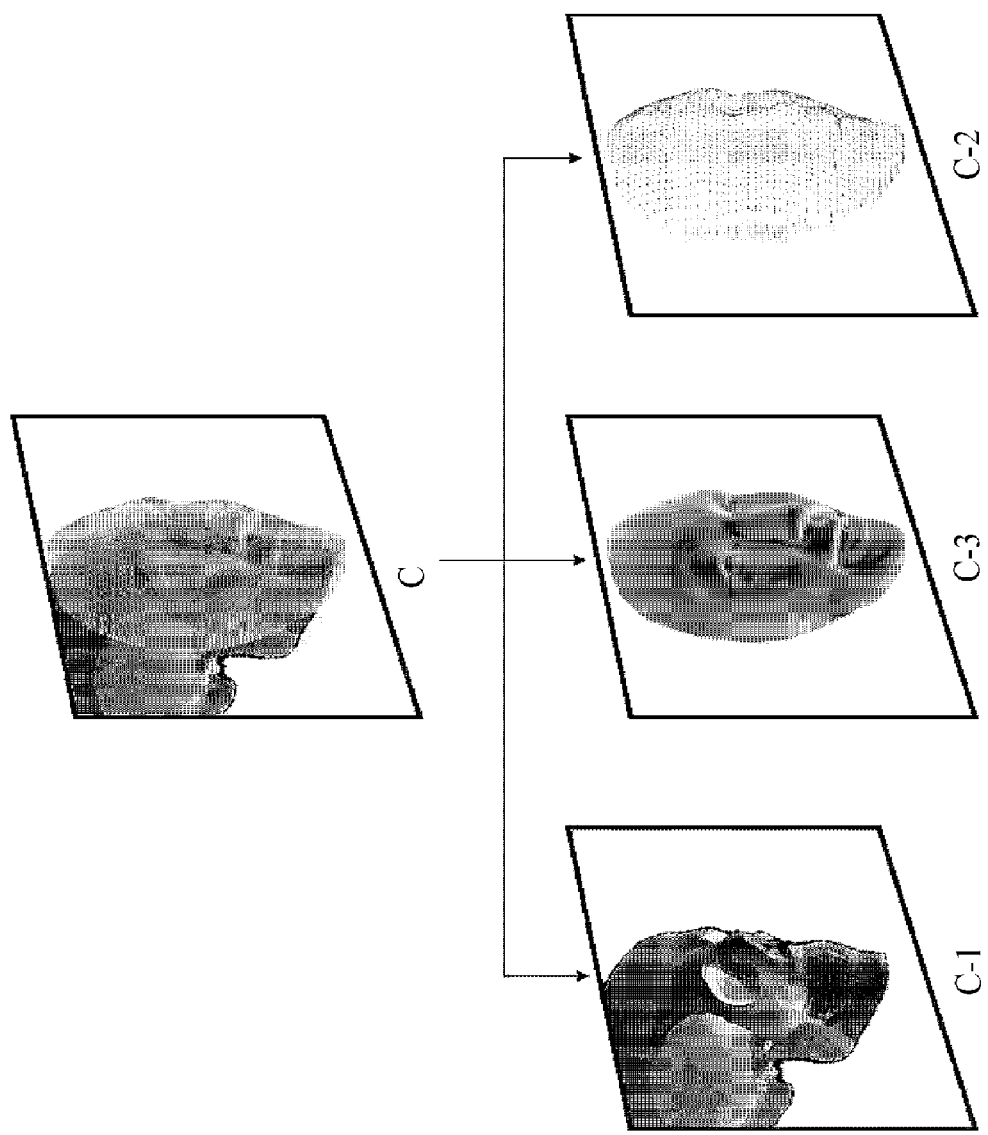
FIG. 2 shows construction of a computer graphics of cranium generated from two-dimensional slice data, a facial computer graphics, and facial surface polygon model.

In addition, when a surface polygon model 1 of structural elements established form two-dimensional slice data of an operated object or body obtained from tomography shoot by left and right cameras of a three-dimensional digital magnifier is directly mapped and tracked in left and right two-dimensional image data D-1-L, D-1-R using computer image processing. In the polygon model 1, any three-dimensional computer graphics of structural elements mapped to structural element texture can be match moved to image of object entity displayed on the binocular image display device. FIG. 2 shows anatomical elements of operated object, bone surface data computer graphics C-1, skin surface computer graphics C-2, epithelium surface polygon model C-3 obtained from two-dimensional slice data complemented by implementing tomography on operated object. For the epithelium surface polygon model C-3, shape constitution of polygon of surface polygon model W-1 constituted by image data of three-dimensional digital magnifier is unified, and number of polygons for an object entity is the smallest number in a range wherein characteristics of the entity can be represented. Accordingly, the polygon constitution utilizes less number of polygons by reducing polygon within polygon model used in texture mapping of bone surface data computer graphics C-1, skin surface computer graphics C-2. The reduction process, by performing the same process in surface polygon model W-1 constituted from stereo measured data obtained by three-dimensional digital magnifier, the unification of the polygon models is remained. The data can be displayed or un-displayed while keeping the positional relation. In addition, when displaying summarized data C or each composition, transparency or hue can be adjusted respectively, thus each anatomic element can be recognized, individually and easily.

Figure 3:
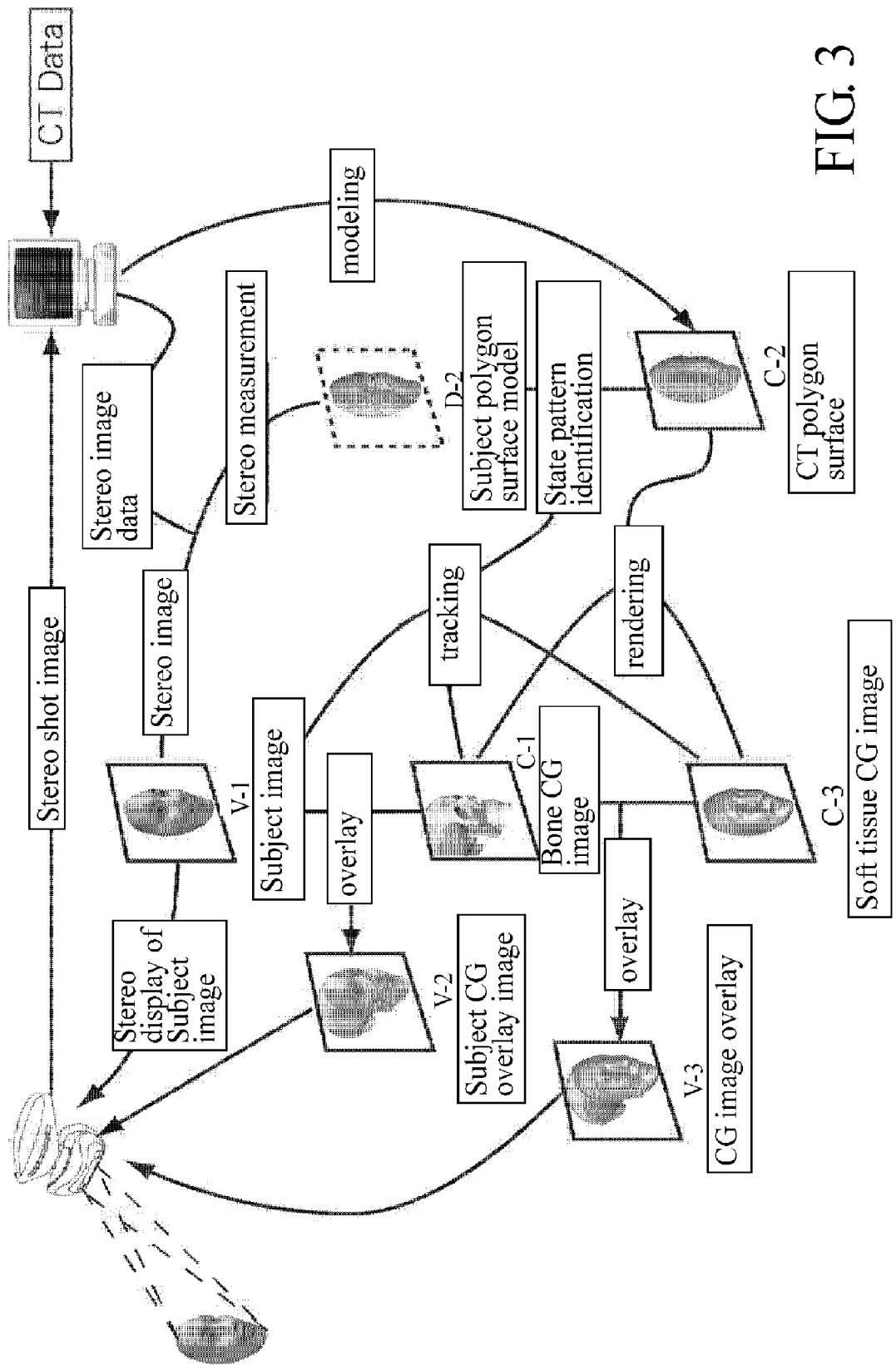
FIG. 3 shows a flow of constructing a computer graphics from two-dimensional sectional data on a three-dimensional digital magnifier monitor.

FIG. 3 shows a flow of unifying data of a three-dimensional digital magnifier monitor and data of sectional image. The three-dimensional digital magnifier, image data of left camera is displayed on an image processing device in one side, while the image data of right camera is displayed on an image processing device on the other side, thus entity can be stereo recognized in a way the same with naked eyes. Accordingly, when implemented separately, as suggested by its name, when returned to a display device in the three-dimensional digital magnifier wherein transparency or hue adjustment of two-dimensional image data of left and right camera of the three-dimensional digital magnifier can be performed individually by a personal computer, it can be used as a magnifier. Two-dimensional image of Left and right camera taken from distance of the stereo-arranged fixed angle and fixed camera of three-dimensional digital magnifier, as shown in FIG. 1, constitutes surface polygon model C-2 by using a personal computer to perform stereo-measurements. The surface polygon model C-2, when recognized by surface polygon model W-1 constituted from CT two-dimensional sectional data shown in FIG. 3, tracks, selectively or not, bone surface data computer graphics C-1 and skin surface computer graphics C-2. Accordingly, when operator puts on the three-dimensional digital magnifier, he may identify computer graphics representing anatomical shapes constituted from sectional image data such as bone surface data computer graphics C-1 and skin surface computer graphics C-2, which are overlaid and displayed in a position the same with a stereo substantial image V-1 in a visional three-dimensional space, and image tracked to substantial image V-1. Accordingly, operation on invisible area of entity 1 and three-dimensionally identification may be implemented, wherein the substantial image V-1 displayed on the three-dimensional digital magnifier and bone surface data computer graphics C-1 and skin surface computer graphics C-2 representing anatomical elements of entity 1 can display invisible area of the entity 1 in the substantial image V-1 by changing transparency of respective layer, the whole computer graphics composition except the substantial image V-1 is displayed, and identified in the a position which is the same with identification by naked eyes.

Figure 4:
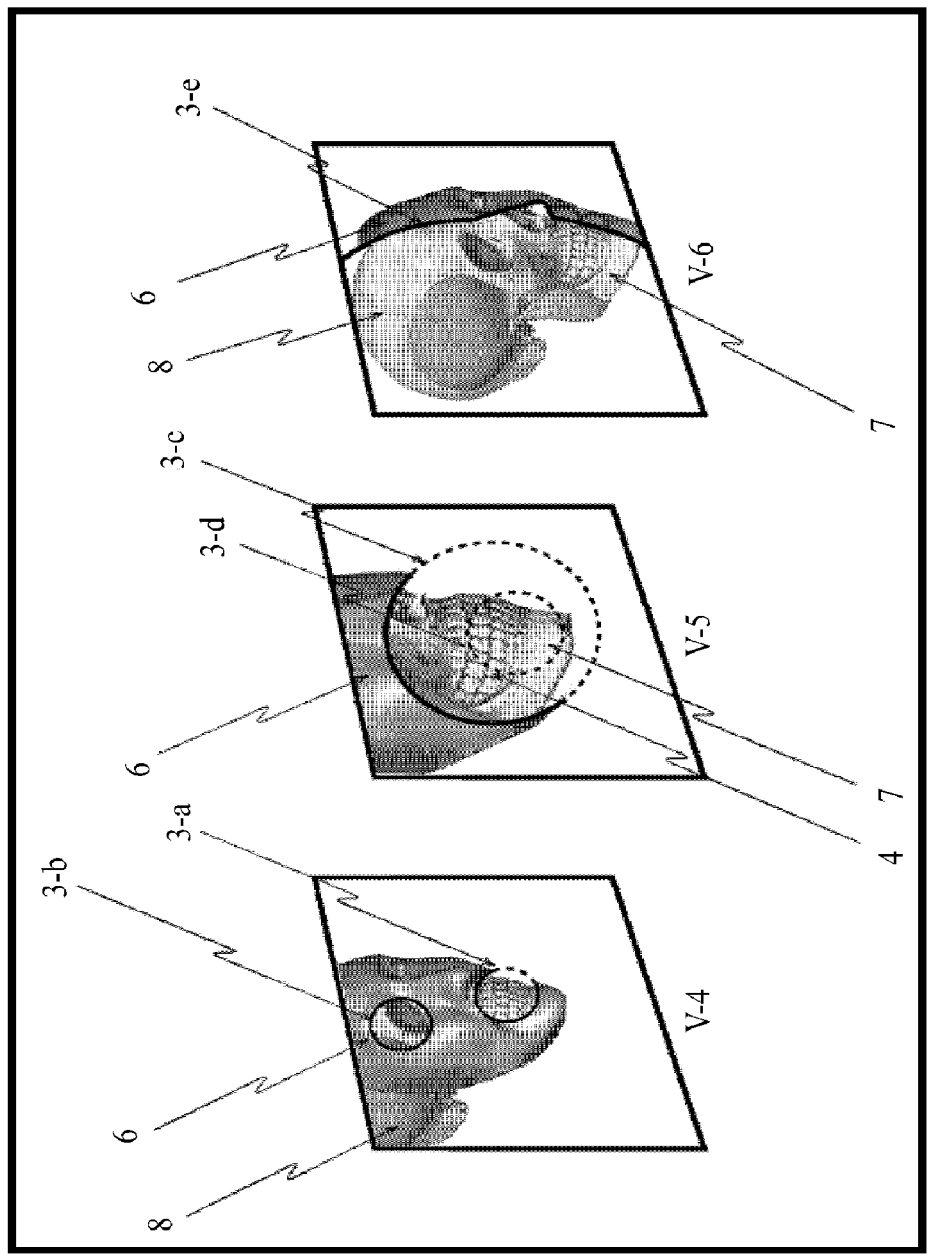
FIG. 4 shows a condition wherein outer computer graphics are taken off to reveal inter computer graphics according to varies settings.
Figure 5:
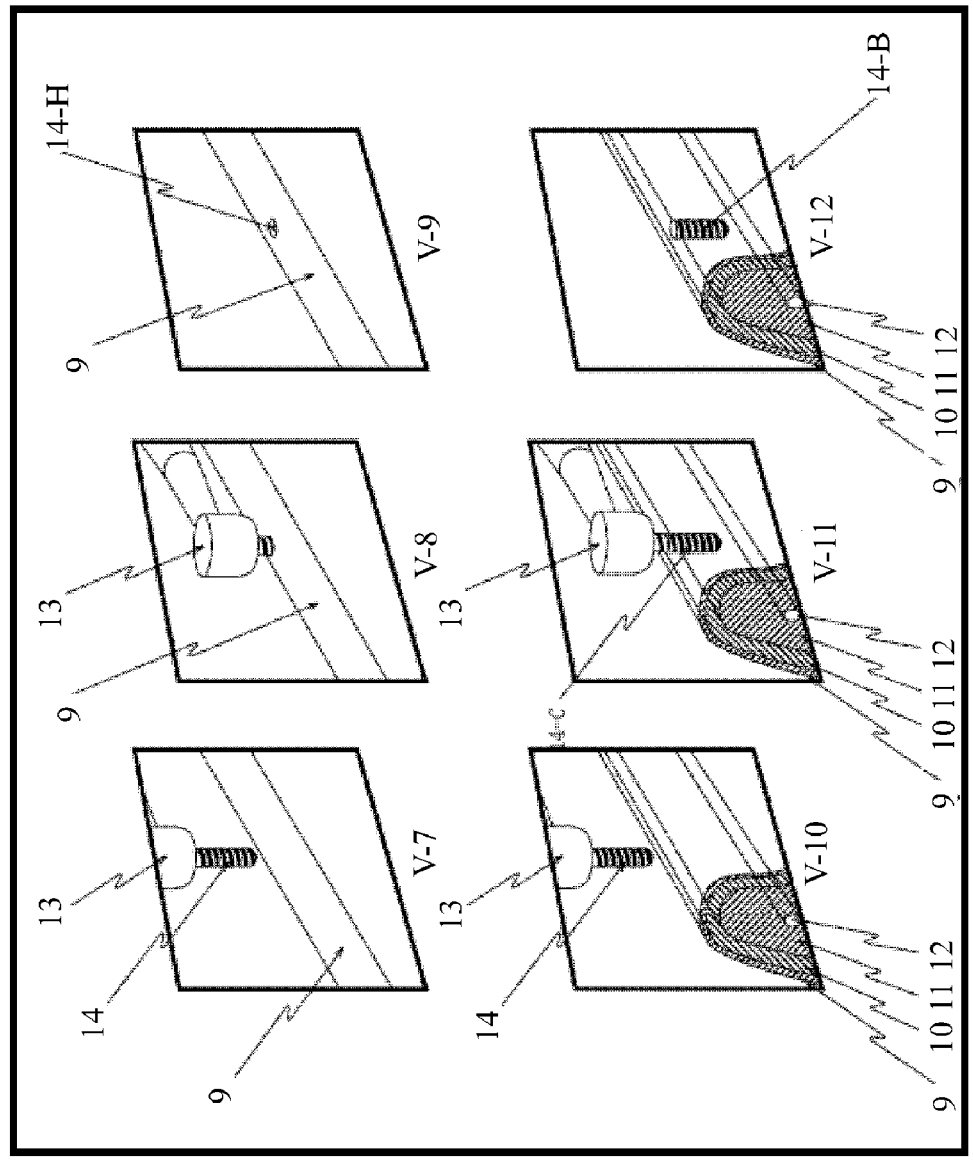
FIG. 5 shows a condition where an implant indentation is formed on an object image displayed on a three-dimensional digital magnifier monitor, and construction of a virtual computer graphical image from a computer graphics of an anatomic structure according to anatomic internal structure on an object image, computer graphics of instruments, and achieved depth of the instruments.

In addition, as shown in FIG. 4 V-4, when the mouth is not open, the tooth CG4-C, inner structure in a lower layer, can be seen by cutting the opaque skin surface computer graphics C-2 by perspective line 3-a. The CG presentation is not only a CG processed by arranging three-dimensional computer graphics sectional image on an object image taken on an image space in advance. In addition, the direction changes when moving any transparent stereo shape using the camera direction as an axis (as the cylinder shown in the exemplary figure) in the direction, and cutting the skin surface computer graphics C-2 by perspective line 3-a, thus the perspective area also moves to 3-b, the same part is divided by Boolean operation, and the bone surface data computer graphics C-1 at the inner layer can be seen through. In addition, if the transparent stereo shape (set as a sphere in this embodiment) is set in a fixed range according to a relative position relationship between the three-dimensional digital magnifier and three-dimensional space, from a status where dentition CG4 at V-4、3-a can be seen through, when the operator wearing the three-dimensional digital magnifier approaches, the perspective area is magnified, area of the dentition CG4 and mandible CG7 can be seen through just like the V-5、3-c. For the perspective line 3-d further magnifying the transparent stereo shape, as shown in V-6, the whole area at the three-dimensional digital magnifier side of the skin surface computer graphics C-2 can be seen through. All of these perspective processes can be respectively configured for each layer, thus layer sectional perspective view is not only the exemplary perspective view of the skin surface computer graphics, but it can also be implemented for each layer, respectively.

When implementing the technique for seeing through layers, as shown in FIG. 4, the teeth implantation without cutting operation can be performed safely. The issues considered for forming teeth implantation cavity comprise: identifying bone amount and shape in the operated area for keeping fine bone structure around the implant neck after the operation; obtaining an implant indentation with deep of tooth crown/dental root more than 1 for evading inferior alveolar nerve. Accordingly, in a traditional operation, alveolar bone is revealed by cutting and peeling mucous membrane bone membrane valve for identifying the bone status; when the implant indentation is formed, measurements of panorama X-rays or CT sectional photograph are used to determine a distance to inferior alveolar nerve, and a blind dolly is performed according to stored X-ray image. In a case that an implant indentation is formed without cutting, as shown by V-7 to V-8 of FIG. 5, when cutting drill 14 cuts into gum soft tissue, direction of the drill and the front point of the drill enters an invisible area. Furthermore, the implant indentation itself formed after V-9 is cut off can not be identified. However, as shown in V-10, when determining status of cortical bone CG from the cortical bone CG 10-C identified in gum soft tissue CG9-C represented by virtual computer graphics, drilling position of the drill 14 is determined, spongy bone CG11-C is cut, as shown in V-11, and the implant indentation can be formed accordingly. At this time, mandible alveolar neural tube CG12-C can also be identified by sight, thus the implant indentation can be safely formed in deep position without damaging nerves. In addition, a three-dimensional identification can be performed to make sure that gum soft tissue CG9-C, cortical bone CG10-C, spongy bone CG11-C are processed by cutting drill 14-C according implant indentation CG14-B as shown by V-12 determined from Boolean operation.

Figure 6:
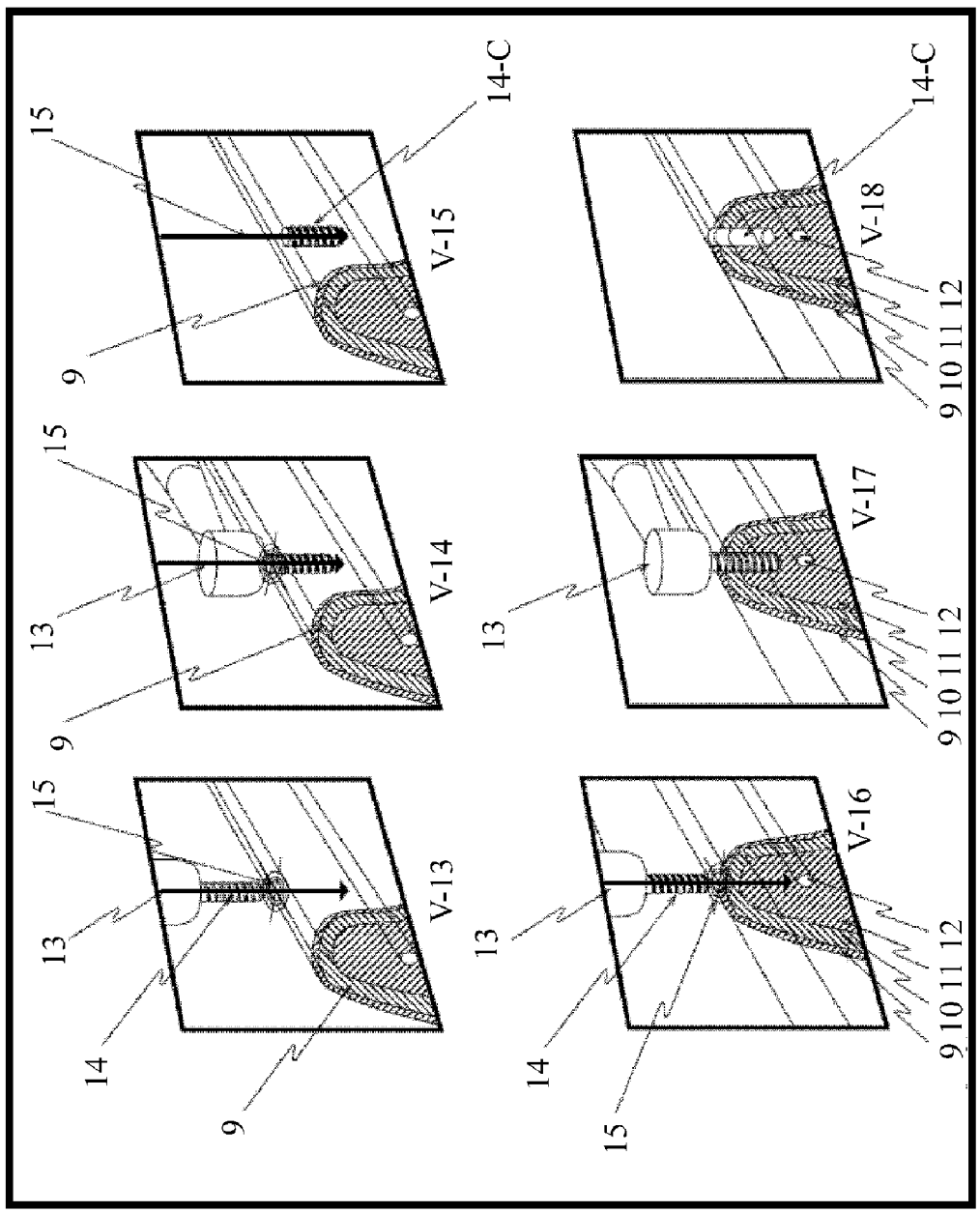
FIG. 6 shows, in addition to the anatomic internal structure, computer graphics of instruments, and virtual computer graphical image shown in FIG. 5, a surgical guide, which is designed on the computer graphics in advance, on an object image, and a condition where the outer computer graphics are taken off to reveal the inner computer graphics.

The operation, as shown in V-13 of FIG. 6, surgical guild CG15-C shows drilling depth and direction, the front point of drill is put on the surgical guild CG15-C on the gum soft tissue CG9-C, as shown in V-14, a drilling process is performed in target direction unless reaching the front point of the surgical guild, the implant indentation is correctly formed at a predetermined implant position while considering anatomical shape of jawbone, bone density, and final patching process. After the implant indentation is formed, implant indentation CG14-B and surgical guild CG15-C can be displayed, if needed, for after-operation valuation. At this time, mandible perspective image displayed by three-dimensional CG is cut by perspective line 3-a shown in V-16、V-17, cutting drill 14-C is verified from the cut sectional direction against surgical guild CG15-C, and a drilling process is performed with verified depth, as shown in V-18. By doing so, operation can be performed, while checking direction and depth of the drilling process, without changing view direction of the operator, from the directions of surgical guild CG15-C and perspective line 3-a.

Figure 7:
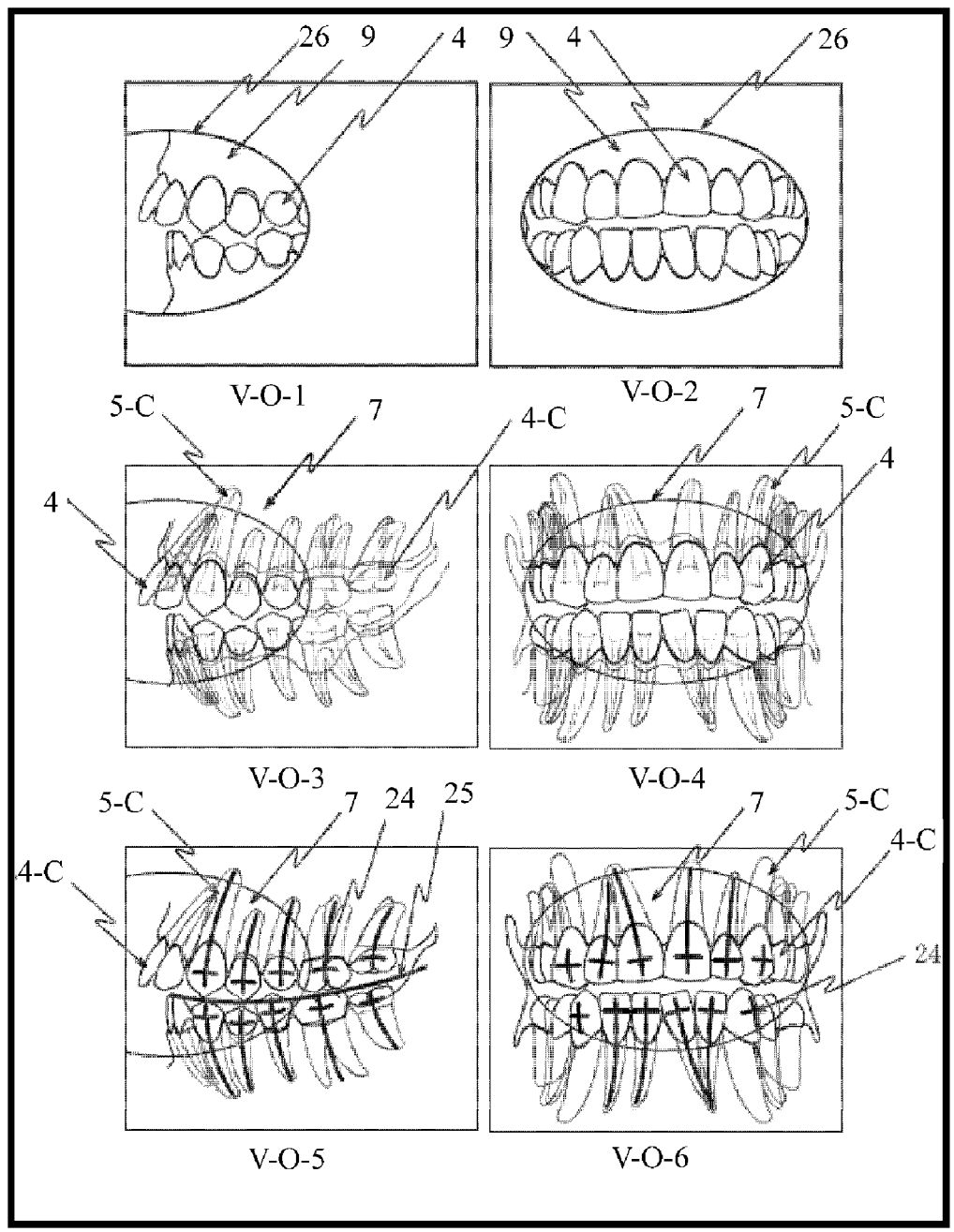
FIG. 7 shows a front-view and side-view image of oral teeth alignment displayed on a three-dimensional digital magnifier monitor; computer graphics generated from two-dimensional sectional data of invisible parts, i.e., a root of a tooth and alveolar process in the image of oral teeth alignment; and a condition wherein bracket position designed on the computer graphics is unified and displayed on the image.
Figure 8:
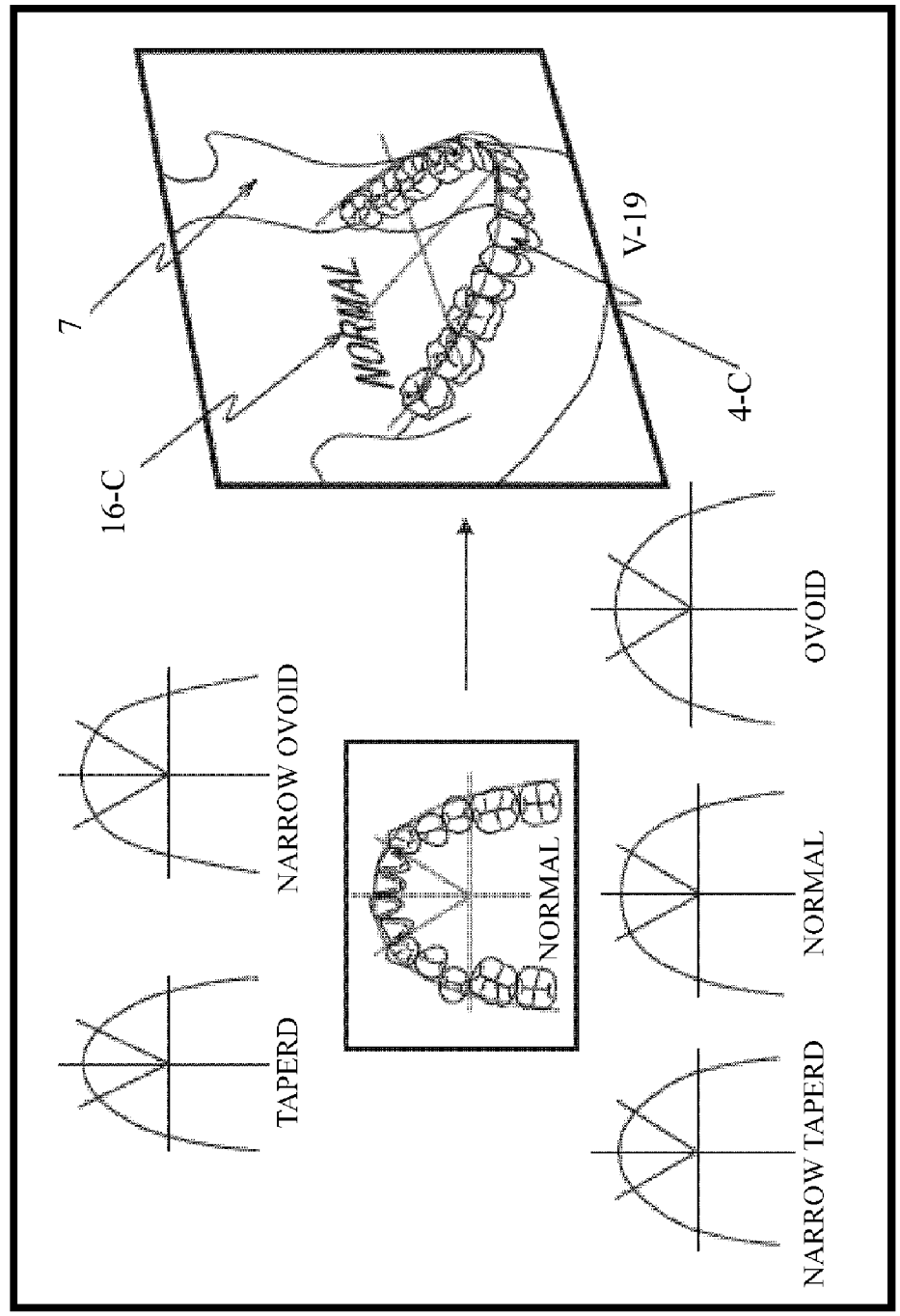
FIG. 8 shows, at a target of orthodontics, ideal arch form of teeth alignment is unified and displayed on teeth alignment image, or teeth alignment computer graphics being three-dimensionally unified at the same position with teeth alignment image.

In the same way, when using three-dimensional digital magnifier to take pictures of oral teeth, it can be identified as V-O-1、V-O-2 of FIG. 7 in response to substantial image observation. When overlaying and displaying tooth CG4-C, dental root CG5-C, gum soft tissue CG9-C, computer graphics layer, and transparent lips 26 layer against teeth substantial image, i.e., anatomical stationary points, as shown in V-O-3 and V-O-4, the status of dental root (opaque area) can be visually identified from the face of the patient. In the field of oral surgery, when removing an impacted tooth, three-dimensional identification of dental root is necessary for safe and correct operation. In addition, in orthodontic treatment, virtual bracket position CG 24 based on direction of dental root and direction of tooth implantation is displayed upon tooth CG4-C, as shown in V-O-5 and V-O-6, thus bracket positioning matching the direction of dental root is possible. During an orthodontic treatment, the teeth movement process can be compared by displaying tooth CG4-C during the treatment process on the current image in an overlaid way. This comparison can be applied in not only individual tooth, but also in valuation of occlusal plane formed by entire dentition. As shown in FIG. 8, status of each tooth compared to a computer graphics ideal arch 16-C determined in a treatment target design period in an orthodontic treatment is displayed on dentition image shown by three-dimensional digital magnifier, or is selectively displayed on dentition tooth CG4-C and lower jawbone CG7, as shown in V-19, thus the current dentition can be evaluated, tooth CG4-C in stored treatment progress is overlaid and displayed, thus treatment step can be re-evaluated and an effective treatment can be realized.

The present invention, causing an invisible area visible, can be applied in surgical treatment or orthodontic treatment, as well as patching occlusal treatment. Conventionally, a complex adjustment is implemented: in order to determine a hinge axis, as a starting point in mandible movement, pantograph is used for mandible manipulation, movement of left and right joint axis is recorded by a recording needle, and a position setting off the position changes is set as a revolving axis. On the other hand, in the present invention, as shown in FIG. 9, substantial image, skull bone CG8 overlaid on the same three-dimensional position, and a temporary computer graphics hinge axis 17-C linking anatomical joint center of and mandible bone CG7 are composed and displayed, computer graphics hinge arc 18-C revolves when manipulating open-close movement against the entity, thus revolution position change of the computer graphics hinge arc 18-C is calculated automatically, and computer graphics hinge axis 17-C is corrected and displayed.

Figure 10:
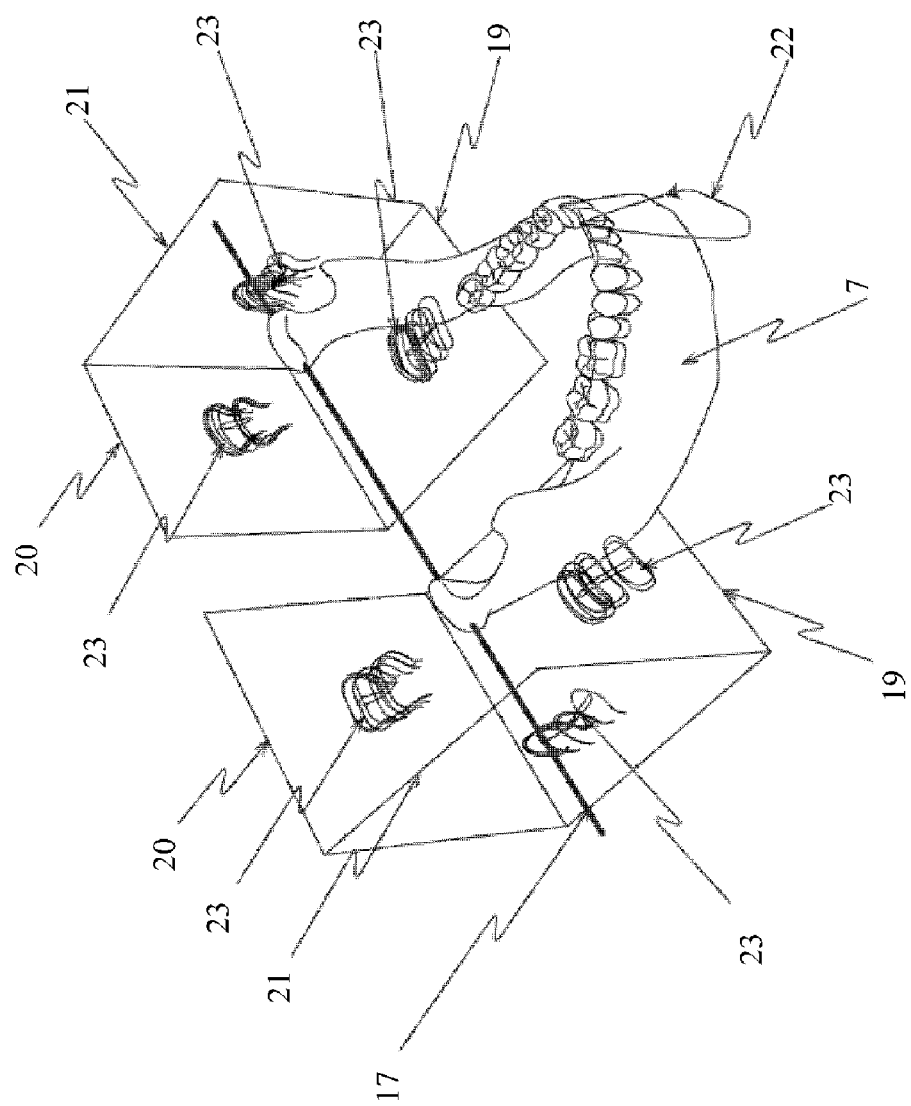
FIG. 10 shows a two-dimensional virtual pantograph of three axis of lower jaw movement from the hinge axis obtained in FIG. 9, and a virtual articulator representing critical path of a mandibular incisor.

FIG. 10 shows a hypothetical pantograph which records the mandibular motion which designates computer graphics hinge axis 17-C which was required in this way as starting point.

In a conditional pantograph, the position of the flag is located outside the face; therefore the presented mandibular movement is not motion track of the joint center of mandibular movement. On the other hand, in the present invention, mandibular movement is presented by three axis in a two-dimensional plant where real hinge axis is used as starting point, thus mandibular head central motion track 23 of left and right joint can be appraised accurately from three axial direction. If marking is performed for joint and tooth CG4-C to lead mandibular critical movement, the motion track is shown as critical path of mandibular incisor 22. Records of the motion track records critical movements, as well as physical mandibular motion during chewing motion, swallowing and speech. Therefore, the virtual occlusion vessel is constructed in the computer, using mandibular head central motion track 23 data, as well as side motion front motion rubbing the dentition. Because this virtual occlusion vessel has expressed the motion of the organism completely, it indicates top and bottom dentition CG on this occlusion vessel, three dimensions CAD can be used in the virtual occlusion vessel in the computer for designing prosthetic appliance which matches to various physiological motions, reproduces chewing cycle and swallowing motion etc for reevaluating functional anatomy of the prosthetic appliance, thus perfect prosthetic treatment can be implemented.

Figure 9:
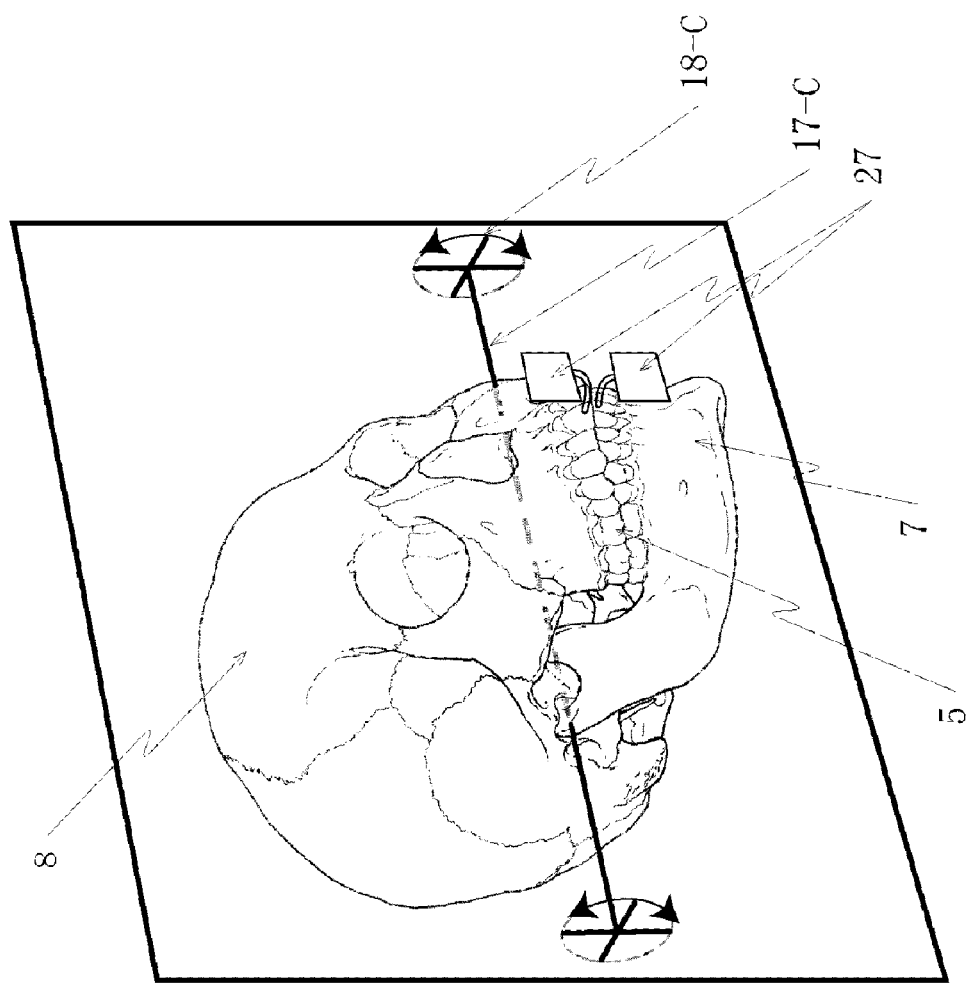
FIG. 9 shows a condition wherein hinge axis of mandible bone head in imaginary movement of mandible bone is unified and displayed on an object image and computer graphics of skull bone and mandible bone three-dimensionally displayed at the same position.

In addition, when this system is implemented in such non-bleeding operation, distributing jaw motion record, diagnosis or orthodontic treatment, the range where the stationary tooth or the bone surface is photographed directly is limited, but when clear vision marker 27 of FIG. 9 is used as polygon model data performing tomography by fixed on top and bottom teeth by a reproducible installation expedient, and is used as the rendering marker of the substantial image, it is possible to obtain a match move function of computer graphics. As for this clear vision marker 27, it can be, even in a state where the lip is closed, installed at the top and bottom tooth, thus jaw motion of physiological motion can be recorded without obstructing the motion of muscle around the oral cavity.

Furthermore, constitution of the picture synthetic layer element of three dimensional digital magnifier operation support system of this invention is not limited to the form of the described embodiment, it is clear that it can add the modification of disassembly or union to the various elements of this invention within the range of the invention.

INDUSTRIAL APPLICABILITY

The three-dimensional digital magnifier operation support system of this invention uses sensing marker installed on image subject and three-dimensional position sensor installed on the camera, and measures relative position changes therebetween, changes displaying direction and display magnifying ratio corresponding to three-dimensional computer graphics image which is relatively fixed to particular image subject image in the shooting space displayed on monitor of effective-eye side of three-dimensional digital magnifier according to relative position changes between the image subject and the camera device, by following the relative position changes between the image subject and the camera occurred in a real three-dimensional space, the entity, i.e., the image subject within the visual field of the camera, and virtual three-dimensional computer graphics image is unified, in the visual field of the camera, the image subject and three-dimensional computer graphics image are unified and displayed independent to the special position changes corresponding to the image subject and camera, as described, the camera and image subject, three-dimensional computer graphics image is displayed by three-dimensional state changes, the three-dimensional computer graphics image is presented, three-dimensionally, on a taken picture with a change the same with real relative position change. Using this system, three-dimensional computer graphics image is fixed to specific subject in camera shooting space displayed on the three-dimensional digital magnifier monitor relative, thus it moves corresponding to three-dimensional position movement of the subject in the actual space, in a case that the three-dimensional digital magnifier on image pickup device side moved, it remains on that position just as the subject, three-dimensional computer graphics image on the view direction the same with the subject projection direction according to changes view direction of the camera is provided, thus, just like perspective glasses, the inside part of the current entity can be identified visually, the whole visual field information can be recognized while recognizing the subject in the three-dimensionally identified image and the three-dimensional computer graphics image, by doing so, it is possible to approach accurately vis-à-vis the invisibility region inside the immediate substance without relying to experience and sensation.

Similarly, a multi-composition image position modification tacking system is provided; in the case that a plurality of subjects exists in a specific space, three-dimensional computer graphics images are arranged to each of the plural subjects, when the subject is an individual of one lump and the subject is deformed, three-dimensional computer graphics images are arranged in a relatively stationary way corresponding to stress force or deformed elements, three-dimensional position sensor installed in the camera uses sensor marker at the respective subject, stress force or deformed respective elements to perform real-time position measurement for relative position changes of the respective subject and the camera, the indicatory direction and indicatory enlargement ratio or display position of the respective three-dimensional computer graphics image, being relatively fixed to in each subject image in the image pickup space which is presented in the monitor of effectiveness eye side of the user, is modified according to three-dimensional relative position changes of subject and the camera, the entity, i.e., the subject in the visual field of the camera and a virtual three-dimensional computer graphics image is unified by tracking the relative position changes of the subject and the camera occurred in real three-dimensional space, in the visual field of the camera, the subject and the three-dimensional computer graphics image is unified and displayed in dependent to special position changes of the subject and camera, and is displayed as three-dimensional state changes of the described camera and subject, three-dimensional computer graphics image, the plurality of entities i.e., the subject in the visual field of the camera, or deforming entity and a plurality or shape-changed virtual three-dimensional computer graphics images are unified, the subject and the three-dimensional computer graphics image is unified and displayed in dependent to special position changes of the subject and camera, in a case where referring to the relationship between respective subject, the respective deformation or changes give impact to each other, simulation relating to state changes of the subject in the real space faithfully regenerates status of three-dimensional computer graphics as deformation of respective element, simulation showing indirect impacts to three-dimensional computer graphics caused by changes of status of picture-taking space is included as merit.

Using this system, three-dimensional computer graphics image which is relative stationary arranged to the respective subject in the image taking space displayed on three-dimensional digital magnifier monitor, is three-dimensionally linked to three-dimensional position movement of each subject in the real space, just like the perspective glasses, inner parts of the current subject can be recognized visually, the whole visual field information can be recognized in a three-dimensional way, while recognizing the respective subject in the three-dimensionally recognized image and the three-dimensional computer graphics image attached to the respective subject. For example, in a case such as complete fracture, by seeing through the connecting circumstance of the fracture region with respect to the image taking space, it is possible, while verifying visually and in spite of the invisible area, to correctly perform the modification without relying on experience or sensation.

In addition, especially in the field of dental prosthesis, when a prosthesis is made based on CAD according to a prosthesis CAD data designed by using the virtual occlusion vessel, it is possible to omit manufacturing process such as impression taking, secondary model production, wax rise and casting, which decreases precision just like the conventional indirect method, and it becomes possible to generate prosthesis with high precision.

The various functions of this invention can be applied in medical field, as well as general industrial field and especially, assembly operation, because range of vision from the invisibility direction which differs from especially line of sight and internal circumstance become be acquired, it is possible to work efficiently in the opaque area.

What is claimed is:

1. A three-dimensional digital magnifier magnifying real operation support system, for regenerating a visual field state the same with a situation in which an operator visually recognizes a subject by naked-eyes or optical magnifier, the system comprises:
   a three-dimensional digital magnifier, comprising:
   a pair of binocular vision image display device, arranged on the gaze of two eyes of the operator, as the minimum constitution;
   stereo arranged camera, installed from a position corresponding to central parts of pupils of the eyes behind the image display device, toward the visual field;
   surface polygon model 2, obtained by stereo measurements of a stereo method using left and right images of the three-dimensional digital magnifier;
   surface polygon model 1 of each constitution component established, in advance, from two-dimensional slice data of operation object or organism obtained by tomography;
   wherein:
   surface polygon model, in the surface polygon model 2 in front visual field image of the three-dimensional digital magnifier, having a three-dimensional shape similar to the surface polygon model 1, is detected by shape pattern recognition, and is then overlaid with the surface polygon model 1;
   virtual three-dimensional volume model computer graphics mapping internal constitution component texture within the surface polygon model 1 is tracked,
   in order to overlay partial or whole subject or organism serving as the operation subject in the visual field of the operator in three-dimensional digital magnifier by three-dimensional volume model computer graphics,
   invisible area of internal structure of an object displayed on the three-dimensional digital magnifier is displayed by pixels of internal constitution components of virtual three-dimensional volume model computer graphics, and the three-dimensional volume model computer graphics image is displayed real-time and changes its layout according to relative three-dimensional position changes of the camera and the object in the image shooting space, simulation relating to state change of subject in a real space presents state of three-dimensional computer graphics overlaid with the subject, and indirect impacts to three-dimensional computer graphics caused by changes of the image shooting space.

2. The three-dimensional digital magnifier magnifying real operation support system of claim 1, wherein:
   by mapping and tracking contour or feature point or line constituting the surface polygon model 1 of each constitution component established, in advance, from two-dimensional slice data of operation object or organism obtained by tomography to the image data taken by respective left and right camera of the three-dimensional digital magnifier,
   any one of the three-dimensional computer graphics of each of the internal constitution mapping to the internal constitution component texture within the surface polygon model 1 is match moved to subject image displayed on the respect left and right binocular vision image display device, simulation corresponding to state change of the subject of image taking in real space is represented as simulation, which presents: state of three-dimensional computer graphics corresponding to internal constitution of subject of image taking, which is displayed with presence, i.e., just as floating on the image taking space, through angle of binocular disparity which is overlaid and displayed upon the subject of stereo vision by the three-digital magnifier, and indirect impact on three-dimensional computer graphics caused by state change of the image taking space.

3. The three-dimensional digital magnifier magnifying real operation support system of claim 1, wherein:
   the three-dimensional computer graphics overlaid and arranged upon the subject of image taking within the image taking space is divided by structural or anatomical structural components to be layerized as separate three-dimensional computer graphics,
   position complementation tracking is performed on each of the layer comprising object image displayed separately or selectively composed multi-composition image,
   when the object image layer is not presented, operation can be directly implemented, just like naked-eye visual field or visual field of optical magnifier, on the subject by vision on virtual three-dimensional computer graphics recognized in sight direction of the three-dimensional digital magnifier, as well as tactile sensation on the subject.

4. The three-dimensional digital magnifier magnifying real operation support system of claim 1, wherein:
   in order to improve visual recognition of the shot image and composed image, shot image or three-dimensional computer graphics, or a composed image position complement tracking is performed to improve visual recognition by setting difference to image data of object, serving as a subject of operation, displayed on the three-dimensional digital magnifier of the operator or organism, which comprises performing image processing on at least one of elements of hue, chrome, lightness, shading and lighting direction, or overlay processing comprising transparent mapping, hidden line elimination wire frame, blinking representation.

5. The three-dimensional digital magnifier magnifying real operation support system of claim 1, wherein:

image of the stereo-arranged camera is respectively displayed on a pair of binocular visual image display device, virtual three-dimensional volume model computer graphics is represented as over layer on image display device of one side of the three-dimensional digital magnifier monitor enabling stereo vision of subject image through left and right angle of binocular disparity, by doing so, the stereo presented invisible are of internal structure of the subject displayed on visual field of three-dimensional digital magnifier is represented by image of internal constitutional element of the virtual three-dimensional volume model computer graphics.

6. The three-dimensional digital magnifier magnifying real operation support system of claim 1, wherein:

two-point measurement is performed, using stereo camera, on four markers set at any position of the subject in the image data of the stereo-arranged camera of the three-dimensional digital magnifier according to optical or digital magnifying ratio of the three-dimensional digital magnifier, a three-dimensional position measurement of the three-dimensional surface polygon model of the subject is performed from the distance between the camera and the subject, and scale of stereo measurement surface data recognition is changed, after image of the subject or the organism is selective detected, mapping and real time tracking is performed on the three-dimensional volume model computer graphics, display position, direction and size of patient anatomical CG and subject (operation instrument CG) are changed, thus is composedly displayed on left and right image display devices of the monitor of the three-dimensional digital magnifier.

7. The three-dimensional digital magnifier magnifying real operation support system of claim 1, wherein:

when using the system, direction of visual field, where three-dimensional computer graphics volume model of a subject or a anatomic specific part of the patient outside display range of monitor of the three-dimensional digital magnifier exist, is represented, especially in the case that high digital magnifying ratio is implemented, the direction, in which the subject or the anatomic specific part of the patient outside display range of monitor of the three-dimensional digital magnifier within the three-dimensional graphics volume model, is represented by causing edge of the image display to blink, or by displaying direction indicator with an arrow, or by showing a frame enclosing image of the displayed portion in entire image wherein the whole is scaled down and displayed in the cutoff screen.

8. The three-dimensional digital magnifier magnifying real operation support system of claim 1, wherein:

when using the system, in the case that each patient anatomical CG volume model, being connected by joint or tissue with registration layout and match move on patient subject upon the three-dimensional digital magnifier, is moved, any of the CG volume model with registration layout and match move on respect patient subject is fixed on a position corresponding to a specific CG volume model at any position upon the movement tracks, and thus can be unified and moves together with the specific CG volume model match moving with the patient subject.

9. The three-dimensional digital magnifier magnifying real operation support system of claim 1, wherein:

when using the system to perform operation, in a case in which a patient subject is incised, cut, and cut off by operation instruments and a shape change is generated accordingly, an operation instrument CG volume model, being processed by registration layout and match move to the operation instrument, is processed by Boolean operation against patient anatomical CG voxel volume mode, patient anatomical CG volume model with registration and match move to the patient subject is processed to incorporate a visual change the same as the operated subject and to display subject invisible part in the patient anatomical CG volume model.

10. The three-dimensional digital magnifier magnifying real operation support system of claim 1, wherein:

when using the system to perform operation, any surface model which is fixed at three-dimensional digital magnifier or area indicator area (wire frame, translucent coloration indicatory or transparency) is overlaid against a patient anatomical CG volume model, in which distance between the three-dimensional digital magnifier and the patient is processed by registration layout and match to a patient subject on the monitor of the three-dimensional digital magnifier, the overlaid part is trimmed off by Boolean operation, cross section of the patient anatomical CG volume model is displayed using preset sectional display range as a unit, or the cross section of the patient anatomical CG volume model, in which processed range changes according to a preset distance between the three-dimensional digital magnifier and the patient is displayed, in real time.

11. The three-dimensional digital magnifier magnifying real operation support system of claim 9, controllable arbitrary surface model area (wire frame representation, translucent coloration representation or transparency) on the six axis direction on the same personal computer interface is overlaid on the virtual three-dimensional volume model computer graphics, which maintains respective relative position relationship of operational field subject or indicator instruments displayed on three-dimensional digital magnifier monitor or a general monitor connecting to the personal computer, the overlaid portion is trimmed off using Boolean operation, cross section of the virtual three-dimensional volume model computer graphics is displayed, at the same time, a third party implements visual instruction, with presence, displaying visual instruction image on an operator visual field stereo image by reflecting on the virtual three-dimensional volume model on the operator display device of the three-dimensional digital magnifier.

12. The three-dimensional digital magnifier magnifying real operation support system of claim 1, surface polygon model 1 of tooth (the crown, dental root), jawbone and maxillofacial, individual parts, which is established from two-dimensional slice data, of operation object or organism obtained beforehand by tomography, is stored respectively, surface polygon model 2 of the individual parts is overlaid on the surface polygon model 2, which measures, by stereo method, the tooth (crown) and oral cavity, and maxillofacial shot by three-dimensional digital magnifier, after surface polygon model 1 of individual parts of the surface polygon model 2 on the front visual field image of the three-dimensional digital magnifier and surface polygon model with three-dimensionally similar shape are detected by respective shape pattern, by performing a tracking on the virtual three-dimensional volume model computer graphics of respective tooth (the crown, dental root) and jawbone which are texture mapping to the polygon model 1, a state of jawbone and tooth and dental root remaining in the jaw bone within an invisible part under an inner mucous membrane within the oral cavity is visually and three-dimensionally recognized using the three-dimensional digital magnifier image display device, and the dentition is recorded as the three-dimensional computer graphics.

13. The three-dimensional digital magnifier magnifying real operation support system of claim 10, treatment target ideal arch dentition image, reconstituting three-dimensional volume model computer graphics of respect tooth mapping three-dimensional surface model and texture, is displayed on three-dimensional digital magnifier monitor according to three-dimensional relative position changes of the maxillofacial and the camera in the oral cavity, treatment target (V.T.O.) is represented and stored.

14. The three-dimensional digital magnifier magnifying real operation support system of claim 1, using the system, pre-designed three-dimensional volume model computer graphics surgical guide is overlaid on object, organism or instrument, serving as the operated subject, mapping texture of a size gauge existing in visual field of operator three-dimensional digital magnifier, three-dimensional approaching direction of the instrument against invisible area of internal structure of the subject displayed on the three-dimensional digital magnifier is displayed by virtual three-dimensional volume model computer graphics surgical guide, and virtual three-dimensional volume model computer graphics surgical guide changes layout and tracking, in real time, following relative three-dimensional position change between camera and subject in image taking space.

15. The three-dimensional digital magnifier magnifying real operation support system of claim 1, using the system, left and right indirect head of the mandibular bone CG volume model with registration layout and match move to the mandibular bone, which is linked by a straight line of virtual butterfly axis, is caused to move, cross sectional line of left and right head of mandible with no position change of persisitens during movement of the virtual butterfly axis is checked on the monitor, at the same time, center of mandible head is determined by setting the cross sectional line, mandible movement from this center is checked on the monitor, locus in accurate condyle path angle is shown in graphic on the monitor, virtual occlusion vessel is established on the monitor by recording the mandible movement as three-dimensional data.

16. The three-dimensional digital magnifier magnifying real operation support system of claim 1, wherein:

stereo method three-dimensional measurement is performed on subject image, which comprises: a passive stereo method by spot lighting method, wherein a spot radiates through a light-emitting diode; or an active stereo method comprising slit light projection method for obtaining shape of the subject by scanning light in order to obtain cross section of the subject by linear light passing a slit generating a corresponding point, or pattern light projection method for determining depth by projecting pattern enabling determination of coordinates of the subject within the camera image, when obtaining surface polygon model 2, front visual field shot image under impact from diode lighting or pattern projection is not represented, virtual three-dimensional volume model computer graphics, tracking to shot operated subject object or organism (subject) image, represents three-dimensional computer graphics image only, operation is performed on the shot object=subject using visual identification of virtual three-dimensional volume model computer graphics, as well as direct or indirect tactile sensation on the shot operation subject object or organism (subject).

17. The three-dimensional digital magnifier magnifying real operation support system of claim 1, wherein:

image data stores respective layer, no matter whether substantial space image of the left and right image taking devices, and three-dimensional computer graphics image data is represented or not on the subject image, the respective layer image is output individually or selectively composedly, and is displayed on three-dimensional digital magnifier or general monitor, three-dimensional computer graphics record data maintaining time-dependent form change is presented on the monitor in a way enabling free manipulation of tilt, pan, zoom and revolution in six revolution axis.

18. The three-dimensional digital magnifier magnifying real operation support system of claim 1, wherein:

the whole three-dimensional computer graphics image scene, using image on subject space covered by subject image of two-dimensional digital magnifier camera as a background, three-dimensional computer graphics image and internal structure thereof, as virtual reality, is processed to make photo real composition image using the two-dimensional image as a light source for lighting.

19. The three-dimensional digital magnifier magnifying real operation support system of claim 1, wherein:

when the substantial space image of the left and right camera and three-dimensional computer graphics image frame is shown alternatively, the respective number of presented frames is adjustable, in the case of overlay representation, the representation ratio, corresponding to left-shot image, right-shot image, or the three-dimensional computer graphics image, of the left and right monitors of the three-dimensional digital magnifier is adjustable, thus image binocular visual identification is adjustable.

20. A method, implemented in a situation where an operator and a helper wear a three-dimensional subject digital magnifier, respectively, comprising:

using the followings:

a three-dimensional digital magnifier, comprising:

a pair of binocular vision image display device, arranged on the gaze of two eyes of the operator, and stereo arranged camera, installed from a position corresponding to central parts of pupils of the eyes behind the image display device, toward the visual field; and surface polygon model 2, obtained by stereo measurements of a stereo method using left and right images of the three-dimensional digital magnifier;

surface polygon model 1 of each constitution component established, in advance, from two-dimensional slice data of operation object or organism obtained by tomography;

wherein:
detecting surface polygon model, in the surface polygon model 2 in front visual field image of the three-dimensional digital magnifier, having a three-dimensional shape similar to the surface polygon model 1, by shape pattern recognition, and then overlaying it with the surface polygon model 1;
tracking virtual three-dimensional volume model computer graphics mapping internal constitution component texture within the surface polygon model 1, or
overlaying partial or whole subject or organism serving as the operation subject in the visual field of the operator in three-dimensional digital magnifier by three-dimensional volume model computer graphics,
by mapping and tracking contour or feature point or line constituting the surface polygon model 1 to the image data taken by respective left and right camera of the three-dimensional digital magnifier, or
by causing any one of the three-dimensional computer graphics of each of the internal constitution mapping to the internal constitution component texture within the surface polygon model 1 to be match moved to subject image displayed on the respect left and right binocular vision image display device,
overlaying partial or whole subject or organism serving as the operation subject in the visual field of the operator in three-dimensional digital magnifier by three-dimensional volume model computer graphics,
wherein:
the method is implemented in a three-dimensional digital magnifier operation support system using for supporting medical surgery or other precision technique presenting invisible area of internal structure of an object presented on the three-dimensional digital magnifier by images of internal constitution components of virtual three-dimensional volume model computer graphics,
virtual three-dimensional computer graphics image is displayed real-time and changes its layout according to relative three-dimensional position changes in the image shooting space of the object and the camera of the three-dimensional substantial digital magnifier worn by the operator and helper, by doing so, simulation relating to state change of subject in a substantial space comprises state of three-dimensional computer graphics overlaid with the subject, and simulation of indirect impacts to three-dimensional computer graphics caused by changes of the image shooting space,
using the pair of three-dimensional substantial digital magnifiers, which are of the same specification and have been synchronized, worn on the operator and the helper, an instructor causes an image tracking three-dimensional volume model computer graphics overlaid to shot subject image and the operator visual three-dimensional shot subject caught by a camera in a visual field direction of three-dimensional substantial digital magnifier worn by the helper to be displayed separately on an monitor screen of the three-dimensional substantial digital magnifier, and
conversely, helper causes an image tracking three-dimensional volume model computer graphics overlaid to shot subject image and the operator visual three-dimensional shot subject caught by a camera in a visual field direction of three-dimensional substantial digital magnifier worn by the instructor to be displayed separately on a monitor screen of the three-dimensional substantial digital magnifier.

* * * * *